United States Patent [19]

Burdeska et al.

[11] 4,297,234
[45] Oct. 27, 1981

[54] BENZOXAZOLYL-STILBENES

[75] Inventors: Kurt Burdeska, Basel; Guglielmo Kabas, Aesch, both of Switzerland

[73] Assignee: Ciba-Geigy Corporation, Ardsley, N.Y.

[21] Appl. No.: 146,960

[22] Filed: May 5, 1980

[30] Foreign Application Priority Data

May 17, 1979 [CH] Switzerland .......... 4596/79

[51] Int. Cl.³ .......... C07D 413/10; C07D 413/14
[52] U.S. Cl. .......... 252/301.24; 252/301.22; 542/435; 542/436; 542/431; 542/464
[58] Field of Search ............ 542/464, 435, 436, 431; 252/301.22, 301.24

[56] References Cited

U.S. PATENT DOCUMENTS 3,684,729  8/1972  Tuite .................................. 542/464
3,732,221  5/1973  Siegrist et al. .................... 542/464
4,061,860 12/1977  Kormany et al. .................. 542/464

FOREIGN PATENT DOCUMENTS

EP-7392  3/1980  European Pat. Off. .

2129816 12/1971  Fed. Rep. of Germany .
2712686  9/1978  Fed. Rep. of Germany .
2730644  1/1979  Fed. Rep. of Germany .

Primary Examiner—Arthur P. Demers
Attorney, Agent, or Firm—Edward McC. Roberts; John P. Spitals

[57] ABSTRACT

Benzoxazolyl-stilbenes of the formula

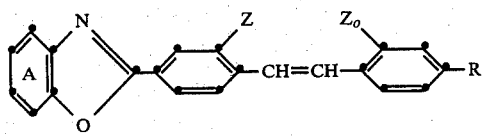

in which R is a 6-membered heterocyclic radical which has 2 nitrogen atoms in the o-position, m-position or p-position relative to one another, and one of Z and $Z_o$ is hydrogen and the other is hydrogen or chlorine, and the benzene nucleus A can carry conventional non-chromophoric substituents, processes for their preparation and their use for the fluorescent brightening of organic material.

14 Claims, No Drawings

BENZOXAZOLYL-STILBENES

The present invention relates to novel benzoxazolyl-stilbenes, processes for their preparation and their use for the fluorescent brightening of organic materials.

The novel benzoxazolyl-stilbenes have the formula

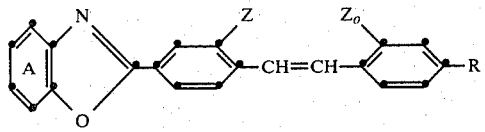

in which R is a 6-membered heterocyclic radical which has 2 nitrogen atoms in the o-position, m-position or p-position relative to one another, and one of Z and $Z_o$ is hydrogen and the other is hydrogen or chlorine, and the benzene nucleus A can carry conventional non-chromophoric substituents.

Examples of non-chromophoric substituents are: halogen atoms; alkyl groups, which can also be substituted, for example by halogen, cyano, hydroxyl, alkoxy, phenoxy, carboxylic acid groups and functional derivatives thereof or aryl radicals, preferably phenyl radicals; cycloalkyl groups; alkenyl groups; alkoxy groups, which likewise can be substituted, for example by hydroxyl, alkoxy, aryl groups, preferably phenyl, phenoxy or cyano; alkenyloxy groups; carboxylic acid groups or sulfonic acid groups and the functional derivatives thereof; sulfonyl groups, for example alkyl- or phenylsulfonyl groups; and aryl or aryloxy groups, preferably phenyl or phenoxy groups, which can be substituted by one or more of the abovementioned radicals. Two adjacent radicals in the ring A can together also form the remaining members of an aromatic carbocyclic ring system, which can also be substituted.

Functional derivatives of sulfonic acid groups and carboxylic acid groups are, in particular, salts, esters and amides. Preferred salts are the alkali metal salts, alkaline earth metal salts, ammonium salts and amine salts, especially the sodium, potassium and ammonium salts. The amides can be unsubstituted on the nitrogen atom or can be monosubstituted or disubstituted on the nitrogen atom, and two substituents together with the nitrogen atom can form the remaining members of a hetero-ring.

6-membered heterocyclic radicals R can be unsubstituted or substituted pyrazines, pyrimidines and pyridazines and also pyridazinones.

Amongst the compounds of the formula (1), benzoxazolyl-stilbenes which are of interest are those of the formula

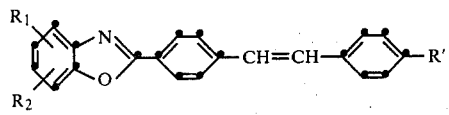

in which $R_1$ is hydrogen, unsubstituted alkyl having 1 to 4 C atoms, or alkyl having 1 to 4 C atoms which is substituted on the terminal C atom by a cyano or XOOC group, in which X is hydrogen, a salt-forming cation or alkyl having 1 to 5 C atoms; alkoxy having 1 to 4 C atoms; unsubstituted phenoxy or phenoxy substituted by 1 or 2 substituents from the group selected from chlorine, methyl and methoxy; chlorine, cyano, —COOX, in which X is as defined; hydroxyalkyl having 1 to 4 C atoms; phenyl; or $SO_2N(Y_1)(Y_2)$, in which $Y_1$ is hydrogen, alkyl having 1 to 6 C atoms, alkyl having 2 to 4 C atoms which is substituted on the terminal C atom by a dialkylamino group which has 1 to 4 C atoms per alkyl moiety and can be quaternised, or alkoxyalkoxy having 3 to 8 C atoms, hydroxyalkyl having 1 to 4 C atoms, alkoxyalkyl having a total of 3 to 8 C atoms, phenyl or benzyl and $Y_2$ is hydrogen, alkyl having 1 to 6 C atoms, hydroxyalkyl having 1 to 4 C atoms or alkoxyalkyl having a total of 3 to 8 C atoms, or $Y_1$ and $Y_2$ together with the nitrogen are a morpholino or piperidino radical; or $R_1$ is alkylsulfonyl having 1 to 6 C atoms, benzylsulfonyl or phenylsulfonyl or together with $R_2$ is a fused phenyl ring, $R_2$ is hydrogen, alkyl having 1 to 4 C atoms, alkoxy having 1 to 4 C atoms or chlorine or together with $R_1$ is a fused phenyl ring and R' is one of the ring systems of the formulae

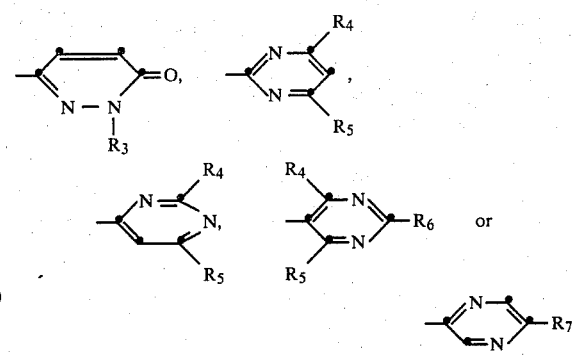

in which $R_3$ is hydrogen, alkyl having 1 to 4 C atoms, unsubstituted phenyl or phenyl substituted by chlorine or methyl, $R_4$ and $R_5$ independently of one another are hydrogen, alkyl having 1 to 4 C atoms, unsubstituted phenyl or phenyl substituted by chlorine or methyl, alkoxy having 1 to 4 C atoms, alkoxyalkoxy having a total of 3 to 8 C atoms, unsubstituted phenoxy or phenoxy substituted by chlorine or methyl, chlorine, alkylthio having 1 to 4 C atoms, phenylthio, alkylamino having 1 to 4 C atoms, dialkylamino having a total of 2 to 8 C atoms, morpholino, piperidino, piperazino, pyrrolidino or anilino, $R_6$ is alkyl having 1 to 4 C atoms, unsubstituted phenyl or phenyl substituted by chlorine or methyl and $R_7$ is alkoxy having 1 to 4 C atoms, alkoxyalkoxy having a total of 2 to 8 C atoms, alkylthio having 1 to 4 C atoms, unsubstituted phenoxy or phenoxy substituted by chlorine or methyl, cycloalkyloxy, alkylthio having 1 to 4 C atoms, unsubstituted phenylthio or phenylthio substituted by chlorine or methyl, alkylamino having 1 to 4 C atoms, dialkylamino having a total of 2 to 8 C atoms, morpholino, piperidino, piperazino, pyrrolidino or anilino.

Cycloalkoxy is preferably cyclopentyloxy or cyclohexyloxy.

Benzoxazolyl-stilbenes of particular interest are those of the formula

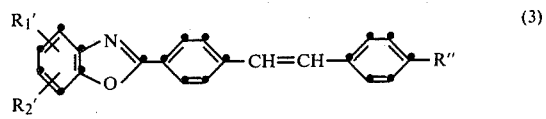

in which $R_1'$ is hydrogen, unsubstituted alkyl having 1 to 4 C atoms or alkyl having 2 to 4 C atoms which is substituted on the terminal C atom by a cyano group; alkoxy having 1 to 4 C atoms; unsubstituted phenoxy or phenoxy substituted by 1 or 2 substituents from the group selected from chlorine, methyl and methoxy; alkoxyalkoxy having 3 to 8 C atoms; cyano; —COOX′, in which X′ is unsubstituted alkyl having 1 to 4 C atoms; phenyl; chlorine; alkylsulfonyl having 1 to 4 C atoms or phenylsulfonyl, $R_2'$ is hydrogen, chlorine, unsubstituted alkyl having 1 to 4 C atoms or unsubstituted alkoxy having 1 to 4 C atoms and R″ is one of the ring systems of the formulae

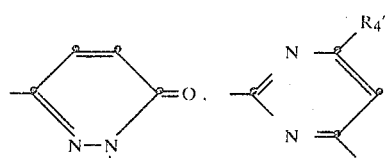

or

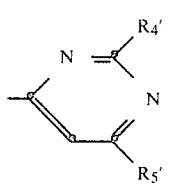

in which $R_3'$ is unsubstituted alkyl having 1 to 4 C atoms or phenyl, $R_4'$ is hydrogen, unsubstituted alkyl having 1 to 4 C atoms, unsubstituted phenyl or phenyl substituted by chlorine or methyl, chlorine, alkoxy having 1 to 4 C atoms, alkoxyalkoxy having a total of 3 to 5 C atoms, unsubstituted phenoxy or phenoxy substituted by chlorine or methyl, alkylthio having 1 to 4 C atoms or phenylthio and $R_5'$ is hydrogen, unsubstituted alkyl having 1 to 4 C atoms, alkoxyalkoxy having 3 to 4 C atoms, alkoxy having 1 to 4 C atoms, unsubstituted phenyl or phenyl substituted by chlorine or methyl, unsubstituted phenoxy or phenoxy substituted by chlorine or methyl, alkylthio having 1 to 4 C atoms, phenylthio or chlorine.

Preferred benzoxazolyl-stilbenes have the formula

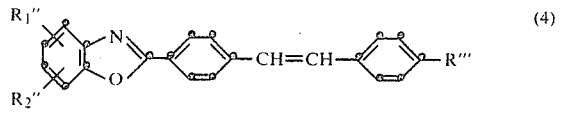 (4)

in which $R_1''$ is hydrogen; unsubstituted alkyl having 1 to 4 C atoms; cyanoethyl; methoxy; phenoxy; chlorine; cyano; alkoxyalkoxy having 3 to 8 C atoms; —COOX′, in which X′ is unsubstituted alkyl having 1 to 4 C atoms; phenyl or alkylsulfonyl having 1 to 3 C atoms, $R_2''$ is hydrogen, unsubstituted alkyl having 1 or 2 C atoms, methoxy or chlorine and R‴ is one of the ring systems of the formulae

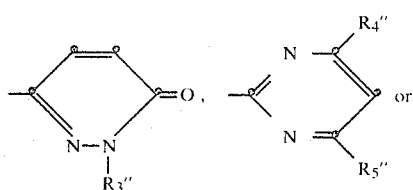 or

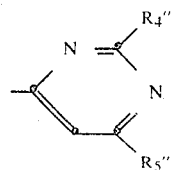

in which $R_3''$ is unsubstituted alkyl having 1 or 2 C atoms, $R_4''$ is hydrogen, methyl, phenyl, alkoxy having 1 to 3 C atoms, methoxyethoxy or phenoxy and $R_5''$ is unsubstituted alkyl having 1 or 2 C atoms, alkoxy having 1 to 3 C atoms or phenoxy.

The benzoxazolyl-stilbenes according to the invention, of the formula (1), can be prepared by diverse methods known per se. Preferably, they are prepared by subjecting a compound of the formula

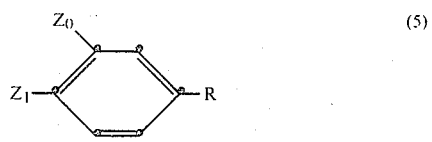 (5)

to a condensation reaction, in an organic solvent and in the presence of basic condensing agents, with a compound of the formula

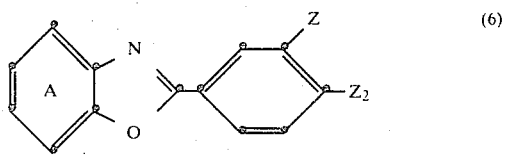 (6)

in which formulae the benzene nucleus A, R, Z and $Z_o$ are as defined above and one of $Z_1$ and $Z_2$ is the OHC group and the other is the grouping

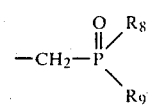

in which $R_8$ and $R_9$ are alkoxy having 1 to 4 C atoms, 5-membered or 6-membered cycloalkyloxy or phenoxy.

The solvents used are advantageously inert solvents, for example hydrocarbons, such as toluene or xylene, or alcohols, such as methanol, ethanol, isopropanol, butanol, glycol, glycol ethers, such as 2-methoxyethanol, hexanol, cyclohexanol or cyclooctanol, and also ethers, such as diisopropyl ether, dioxan or tetrahydrofuran, and also formamides or N-methylpyrrolidone. Dipolar organic solvents such as dimethylformamide and dimethylsulfoxide are particularly suitable.

Suitable condensing agents are strongly basic compounds, such as alkali metal hydroxides and alkaline earth metal hydroxides, alkali metal amides and alkaline earth metal amides, alkali metal alcoholates and alkaline earth metal alcoholates, for example potassium hydroxide, sodium hydroxide, potassium tert.-butylate, sodium amide or sodium methylate, and also the alkali metal compounds of dimethylsulfoxide and alkali metal hydrides and in some cases alkali metal dispersions.

The reaction is preferably carried out in the temperature range of 0° to 100° C. The compounds according to the invention are also obtained when the corresponding quaternary phosphonium salts, for example the triphenylphosphonium salts, are employed in place of phosphono compounds (5) and (6), and these salts are subjected to the condensation reaction with the aldehydes (6) or (5) via the phosphorylene intermediates.

It is, of course, also possible to subject the reaction products obtained from the above processes to further conversion reactions known per se, such as halogenation reactions, functional modifications of carboxyl groups, the introduction of chloromethyl groups or the replacement of halogen atoms by cyano groups.

However, compounds of the formula (1) can also be prepared by other processes known per se. Thus, it is possible to react a Schiff's base of the formula

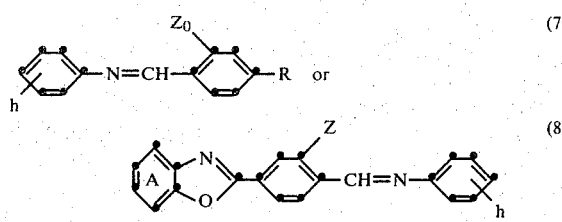

in which the benzene nucleus A can be substituted as defined above, R, Z and $Z_o$ are as defined above and h is advantageously hydrogen or chlorine, with a methyl compound of the formula

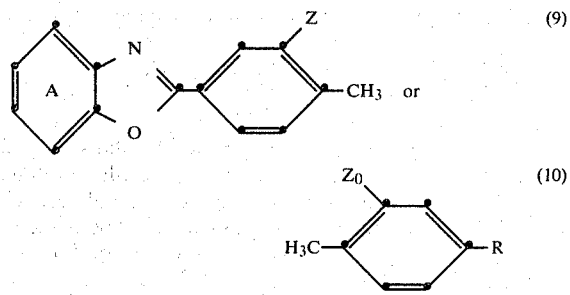

in which A, R, Z and $Z_o$ are as defined above, in the presence of a strongly basic alkali metal compound in dimethylformamide as the reaction medium. In this specification, strongly basic alkali metal compounds are to be understood as meaning those compounds of the alkali metals which have a base strength at least approximately equal to that of lithium hydroxide. The compounds can accordingly be compounds of lithium, sodium, potassium, rubidium or caesium of, for example, the alcoholate, hydroxide or strongly basic ion exchanger type. Compounds advantageously used are potassium compounds having the composition

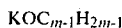

$KOC_{m-1}H_{2m-1}$ in which m is an integer from 1 to 6, for example potassium hydroxide or potassium tertiary butylate. In the case of alkali metal alcoholates, the reaction must be carried out in a virtually anhydrous medium, whilst in the case of alkali metal hydroxides water contents of up to 25% (for example contents of water of crystallisation) are permissible. In the case of potassium hydroxide, a water content of up to about 10% has proved advantageous. Examples of other alkali metal compounds which can be used are: sodium methylate, sodium hydroxide, lithium hydroxide, rubidium hydroxide, caesium hydroxide and the like. Of course, it is also possible to use mixtures of such bases for the reaction.

Advantageously, the compounds of the formula (9) or (10) are reacted with the Schiff's base of the formula (7) or (8) in equivalent amounts, so that there is not a substantial excess of either component. Advantageously, the alkali metal compound is used in at least the equivalent amount, i.e. at least 1 mol of a compound containing, for example, a KO group is used per mol of Schiff's base. If potassium hydroxide is used, this is preferably employed in the 4-fold to 8-fold amount. In general, the reaction can be carried out at temperatures in the range between about 10° and 150° C. If alcoholates are used as the potassium compound for the reaction, it is generally not necessary to supply heat. The procedure is, for example, to add the Schiff's base of the formula (7) or (8) to the mixture of the compound of the formula (9) or (10), the solvent and the potassium alcoholate, advantageously with stirring and with the exclusion of air, at a temperature between 15° and 30° C., whereupon the reaction readily takes place, the temperature rising slightly. When potassium hydroxide is employed, it is frequently necessary to carry out the reaction at a higher temperature. For example, the reaction mixture is slowly warmed to 30° to 100° C. and then kept at this temperature for some time, for example ½ to 2 hours. The end products can be isolated from the reaction mixture by conventional methods known per se.

The compounds according to the invention exhibit a pronounced fluorescence in solution or dispersion. They can be used for the fluorescent brightening of a wide variety of synthetic, regenerated man-made or natural organic materials, or substances which contain such organic materials.

Without any restriction being implied by the following classification, examples of organic materials which can undergo fluorescent brightening are:

I. Synthetic organic materials of high molecular weight:

(a) Polymerisation products based on organic compounds containing at least one polymerisable carbon-carbon double bond, i.e. their homopolymers or copolymers as well as their after-treatment products, for example crosslinking, grafting or degradation products, polymer blends, or products obtained by modification of reactive groups, for example polymers based on α,β-unsaturated carboxylic acids or derivatives of such carboxylic acids, especially on acrylic compounds (for example acrylates, acrylic acid, acrylonitrile, acrylamides and their derivatives or their methacrylic analogues), on olefin hydrocarbons (for example ethylene, propylene, styrenes or dienes and also ABS polymers) and polymers based on vinyl and vinylidene compounds (for example vinyl chloride, vinyl alcohol and vinylidene chloride), (b) Polymerisation products which can be obtained by ring opening, for example polyamides of the polycaprolactam type, and also polymers which are obtainable either by polyaddition or by polycondensation, such as polyethers or polyacetals, (c) Polycondensation products or precondensates based on bifunctional or polyfunctional compounds with condensable groups, the homocondensation and co-condensation products, and after-treatment products thereof, for example polyesters in particular saturated polyesters (for example polyesters of ethylene glycol terephthalic acid) or unsaturated polyesters (for example maleic acid/dialcohol polycondensates and their crosslinking products with copolymerisable vinyl monomers), unbranched and branched polyesters (also including those based on polyhydric alcohols, for example alkyd resins), polyamides (for example hexamethylenediamine adipate), maleic resins, melamine resins, the precondensates and analogues thereof, polycarbonates and silicones, and (d) Polyaddition products, such as polyurethanes (crosslinked and uncrosslinked) and epoxide resins.

II. Regenerated man-made organic materials, for example cellulose esters of varying degrees of esterification (so-called 2½-acetate or triacetate) or cellulose ethers, regenerated cellulose (viscose or cuprammonium cellulose), or their after-treatment products, and casein plastics.

III. Natural organic materials of animal or vegetable origin which are based on cellulose, such as cotton or linen.

The organic materials which are to undergo fluorescent brightening can be in the most diverse states of processing (raw materials, semi-finished goods or finished goods). On the other hand, they can be in the form of structures of the most diverse shapes, for example predominantly three-dimensionally expanded structures, such as sheets, profiles, injection mouldings, various machined articles, chips, granules or foams, and also predominantly two-dimensional structures, such as films, foils, lacquers, coverings, impregnations and coatings, or predominantly one-dimensional bodies, such as filaments, fibres, flocks and wires. The said materials can, on the other hand, also be in an unshaped state, in the most diverse homogeneous or inhomogeneous forms of diversion, as for example in the form of powders, solutions, emulsions, dispersions, latices, pastes or waxes.

Fibrous materials can be, for example, in the form of endless filaments (stretched or unstretched), staple fibres, flocks, hanks, textile filaments, yarns, threads, non-wovens, felts, waddings, flocked structures or woven textile or bonded textile fabrics, knitted fabrics and papers, cardboards or paper pulps.

The compounds according to the invention are of importance, inter alia, for the treatment of organic textile materials, especially woven textile fabrics. If fibres, which can be in the form of staple fibres or endless filaments or in the form of hanks, woven fabrics, knitted fabrics, non-wovens, flocked substrates or bonded fabrics, are to be subjected to fluorescent brightening according to the invention, this is advantageously effected in an aqueous medium in which the compounds in question are present in a finely divided form (suspensions, so-called microdispersions or, in some cases, solutions). If desired, dispersing agents, stabilisers, wetting agents and further assistants can be added during the treatment.

Depending on the type of fluorescent brightener compound used, it can prove advantageous to carry out the treatment in a neutral or alkaline or acid bath. The treatment is usually carried out at temperatures of about 20° to 140° C., for example at the boiling point of the bath or near it (about 90° C.). Solutions or emulsions in organic solvents can also be used for the finishing of textile substrates, as is practised in the dyeing industry in so-called solvent dyeing (pad-thermofixation or exhaust dyeing processes in dyeing machines).

The compounds according to the invention can further be added to, or incorporated in, the materials before or during their shaping. Thus, they can, for example, be added to the compression moulding composition or injection moulding composition during the manufacture of films, sheets (for example incorporated in polyvinyl chloride in a roll mill at elevated temperature) or mouldings.

If the shaping of man-made synthetic or regenerated man-made organic materials is effected by spinning processes or from spinning solutions/melts, the compounds according to the invention can be applied by the following processes:

Addition to the starting substances (for example monomers) or intermediates (for example precondensates or prepolymers), ie. before or during the polymerisation, polycondensation or polyaddition, Sprinkling in powder form on polymer chips or granules for spinning solutions/melts, Bath dyeing of polymer chips or granules for spinning solutions/melts, Metered addition to spinning melts or spinning solutions, and Application to the spun tow before stretching.

The compounds according to the invention can, for example, also be employed in the following use forms:

(a) In mixtures with dyes (shading) or pigments (coloured pigments or especially, for example, white pigments) or as an additive to dyebaths, printing pastes, discharge pastes or reserve pastes, or for the after-treatment of dyeings, prints or discharge prints, (b) In mixtures with carriers, wetting agents, plasticisers, swelling agents, antioxidants, light stabilisers, heat stabilisers and chemical bleaching agents (chlorite bleach or bleaching bath additives), (c) In mixtures with crosslinking agents or finishing agents (for example starch or synthetic finishers), and in combination with a wide variety of textile finishing processes, especially resin finishes (for example creaseproof finishes such as "wash-and-wear", "permanent-press" or "no-iron"), as well as flameproof finishes, soft-handle finishes, anti-soiling finishes or antistatic finishes, or antimicrobial finishes, (d) Incorporation of the fluorescent brightening agents into polymeric carriers (polymerisation, polycondensation or polyaddition products), in the dissolved or dispersed form, for use, for example, in coating agents, impregnating agents or binders (solutions, dispersions and emulsions) for textiles, non-wovens, paper and leather, (e) As additives to master batches, (f) As additives to a wide variety of industrial products in order to render these more marketable (for example improving the appearance of soaps, detergents and pigments), (g) In combination with other substances which act as fluorescent brighteners, (h) In spinning bath preparations, i.e. as additives to spinning baths which are used for improving the slip for further processing of synthetic fibers, or from a special bath before stretching of the fibre, (i) As scintillators for various purposes of a photographic nature, for example for electrophotographic reproduction or supersensitising, and (j) Depending on the substitution, as laser dyes.

If the brightening process is combined with textile treatment or finishing methods, the combined treatment can in many cases advantageously be carried out with the aid of appropriate stable preparations which contain the fluorescent brightener compounds in a concentration such that the desired white effect is achieved.

In certain cases, the fluorescent brightening agents are made fully effective by an after-treatment. This can be, for example, a chemical treatment (for example an acid treatment), a thermal treatment (for example heat) or a combined chemical/thermal treatment. Thus, for example, the appropriate procedure to follow in the fluorescent brightening of a number of fibre substrates, for example polyester fibres, with the fluorescent brightening agents of the present invention, is to impregnate these fibers with the aqueous dispersions (or, if desired, also solutions) of the fluorescent brightening agents at temperatures below 75° C., for example at room temperature, and to subject them to a dry heat treatment at temperatures above 100° C., it being generally advisable additionally to dry the fibrous material beforehand at a moderately elevated temperature, for example at not less than 60° C. to about 130° C. The heat treatment in the dry state is then advantageously carried out at temperatures between 120° and 225° C., for example by heating in a drying chamber, by ironing within the specified temperature range or by treatment with dry, superheated steam. The drying and dry heat treatment can also be carried out in immediate succession or can be combined in a single operation.

The amount of the novel fluorescent brightening agent to be used according to the invention, based on the weight of the material to be subjected to fluorescent brightening, can vary within wide limits. A marked and lasting effect can be obtained even with very small amounts and in certain cases, for example, with amounts of 0.0001 percent by weight. However, it is also possible to use amounts of up to about 0.8 percent by weight and in some cases of up to about 2 percent by weight. For most practical purposes, it is preferable to use amounts between 0.0005 and 0.5 percent by weight.

For various reasons it is frequently advantageous not to use the fluorescent brightening agents by themselves, i.e. as the pure substances, but in admixture with a wide variety of assistants and extenders, for example anhydrous sodium sulfate, sodium sulfate decahydrate, sodium chloride, sodium carbonate, alkali metal phosphates, such as sodium orthophosphate, potassium orthophosphate, sodium pyrophosphate, potassium pyrophosphate and sodium tripolyphosphates or potassium tripolyphosphates, or alkali metal silicates.

In the examples, percentages are always by weight, unless indicated otherwise. Melting points and boiling points are uncorrected, unless indicated otherwise.

EXAMPLE 1:

10.8 g of 2-(4-diethoxyphosphorylmethylphenyl)-4-methylbenzoxazole, 6.43 g of 1-methyl-3-(4-formylphenyl)-pyridazinone and 120 ml of dimethylformamide are warmed to 40° C. 2.1 g of sodium methylate are introduced into the resulting solution at 40°-45° C. in the course of 10 minutes. The reaction mixture is stirred for a further 3 hours at this temperature, then cooled to room temperature, rendered weakly acid with formic acid and then stirred into 800 ml of water. The product which has precipitated is filtered off, washed with water and with methanol and dried in vacuo. 11.1 g of the compound of the formula

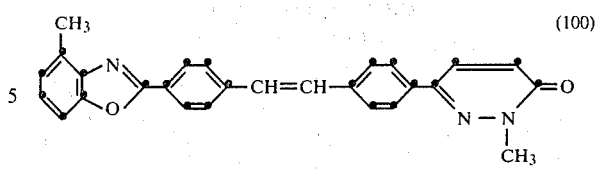

are obtained. The product crystallises from chlorobenzene, with the addition of bleaching earth, in the form of yellow crystals with a melting point of 244°-245° C. The 1-methyl-3-(4-formylphenyl)-pyridazinone required as the starting material is prepared in the following way.

110 g of 1-methyl-3-(4-methylphenyl)-pyridazinone and 700 ml of carbon tetrachloride are heated to 70° C. A mixture of 3.5 g of dibenzoyl peroxide and 103.3 g of N-bromosuccinimide are now introduced into the resulting solution at 70°-75° C. in the course of 40 minutes, whilst at the same time irradiating with a 500 watt lamp. The mixture is then stirred under reflux for a further 3 hours. The succinimide is then filtered off at 65° C., the filter cake is washed with 100 ml of hot carbon tetrachloride and the filtrate is evaporated to dryness. The residue is stirred with 100 ml of methanol whilst still warm, whereupon crystallisation takes place. After cooling, the product is filtered off and washed with a little cold methanol. After drying in vacuo at 80° C., 115.2 g of the compound of the formula

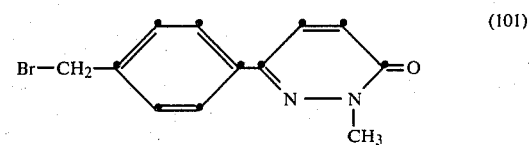

are obtained. The product crystallises from methanol in the form of colourless crystals with a melting point of 135°-136° C.

35.9 g of 2-nitropropane are allowed to run into a solution of 7.13 g of sodium in 550 ml of anhydrous ethanol in the course of 10 minutes. The resulting solution is stirred for a further 4 hours at room temperature, during which time some of the sodium salt of 2-nitropropane precipitates out. 86.52 g of 1-methyl-3-(4-bromomethylphenyl)-pyridazinone and 200 ml of dimethylformamide are now added successively to the resulting suspension. The mixture is then heated to 60°-65° C. and stirred at this temperature for 1½ hours. In order to bring the reaction to completion, the mixture is stirred for a further 14 hours at room temperature. The reaction mixture is now cooled to 5° C. and the product which has precipitated out is filtered off and washed successively with methanol, water and methanol and dried in vacuo at 80° C. This yields 58.6 g of the compound of the formula

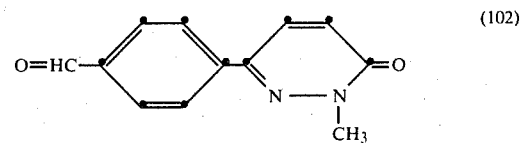

which has a melting point of 201°-203° C. 1-Ethyl-3-(4-formylphenyl)-pyridazinone would also be obtained in the same manner from 1-ethyl-3-(4-methylphenyl)-pyridazinone (melting point 94°-96° C.).

The compounds of the formula

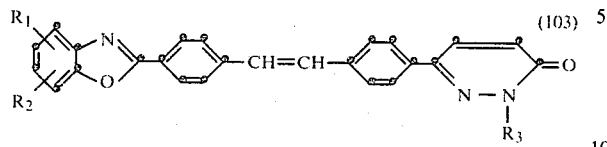 (103)

listed in Table I are obtained from the corresponding starting materials by an analogous procedure.

TABLE I

| Compound No. | $R_1$ | $R_2$ | $R_3$ | Melting point °C. |
|---|---|---|---|---|
| 104 | 5-$CH_3$ | 7-$CH_3$ | —$CH_3$ | 273-275 |
| 105 | 5-$CH_3$ | 7-$CH_3$ | —$C_2H_5$ | 237-238 |
| 106 | 7-Cl | H | —$CH_3$ | 274-276 |
| 107 | 7-Cl | H | —$C_2H_5$ | 238-239 |
| 108 | 7-$CH_3$ | H | —$CH_3$ | 261-262 |
| 109 | 4-$CH_3$ | H | —$C_2H_5$ | 226-227 |
| 110 | 4-$OCH_3$ | H | —$CH_3$ | 276-277 |
| 111 | 5-$CH_2$—$CH_2$—CN | H | —$CH_3$ | 273-274 |
| 112 | 5-$CH_2$—$CH_2$—CN | H | —$C_2H_5$ | 252-253 |

EXAMPLE 2:

1.76 g of sodium methylate are added in the course of 15 minutes, at 40° C., to a solution of 10 g of 2-(4-diethoxyphosphorylmethylphenyl)-5-tert.-butylbenzoxazole and 6.1 g of 4,6-dimethoxy-2-(4-formylphenyl)-pyrimidine in 100 ml of dimethylformamide. The reaction mixture is stirred for a further 3 hours at 40°-45° C. and then poured into 1,000 ml of ice-water and the resulting mixture is rendered weekly acid with formic acid. The product which has precipitated is filtered off, washed with water and methanol and dried. 11 g of the crude product of the formula

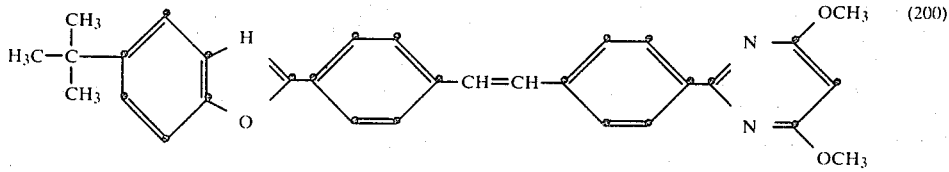 (200)

are obtained. Greenish-tinged yellow crystals with a melting point of 184°-185° C. are obtained by recrystallisation from benzene/cyclohexane (1:1).

The 4,6-dimethoxy-2-(4-formylphenyl)-pyrimidine required for the reaction is prepared in the following way:

115.2 g of 4,6-dimethoxy-2-(4-methylphenyl)pyrimidine and 500 ml of carbon tetrachloride are heated to 70° C. A mixture of 0.5 g of dibenzoyl peroxide, 1 g of azoisobutyronitrile and 90.8 g of N-bromosuccinimide is then introduced into the solution at 70°-75° C. in the course of 30 minutes, whilst at the same time irradiating with a 500 watt lamp.

In order to bring the reaction to completion, the reaction mixture is refluxed for a further 2½ hours. The succinimide is then filtered off at 65° C. and the filtrate is evaporated to dryness. 144 g of the crude product of the formula

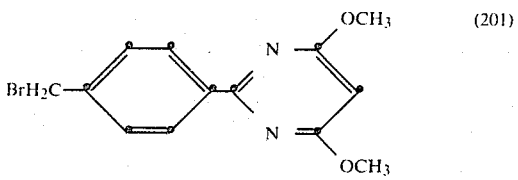 (201)

are obtained. The product can be purified by recrystallisation from ethanol/ethylene glycol monomethyl ether (1:1). (Melting point 132°-134° C.).

38.22 g of 2-nitropropane are allowed to run into a solution of 7.59 g of sodium in 500 ml of anhydrous ethanol. The reaction mixture is then stirred for 5 hours at room temperature. After adding 102 g of 4,6-dimethoxy-2-(4-bromomethylphenyl)-pyrimidine and 350 ml of dry dimethylformamide, the mixture is heated to 60°-65° C. and stirred at this temperature for 1½ hours. It is then allowed to cool to room temperature overnight, with stirring. The mixture is cooled to 5° C. in order to precipitate all of the product, which is then filtered off, washed with ethanol and dried in vacuo at 70° C. This yields 53.7 g of the compound of the formula

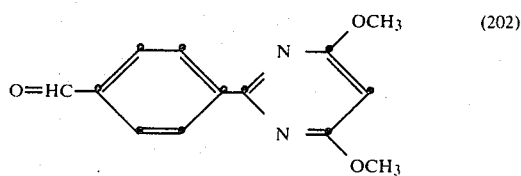 (202)

which has a melting point of 128°-130° C. A further 15 g of aldehyde can be obtained from the filtrate by precipitating with water.

4,6-Diethoxy-2-(4-formylphenyl)-pyrimidine (melting point 87°-88° C.) and 4,6-diphenoxy-2-(4-formylphenyl)pyrimidine (melting point 143°-145° C.) were obtained by the same reaction procedure.

The compounds of the formula

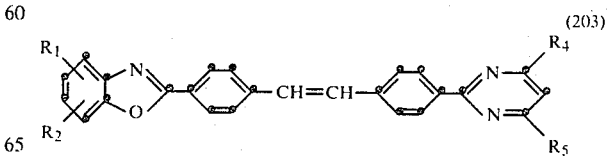 (203)

listed in Table II are obtained from the corresponding starting materials by an analogous procedure.

TABLE II

| Compound No. | R$_1$ | R$_2$ | R$_4$ | R$_5$ | Melting point °C. |
|---|---|---|---|---|---|
| 204 | 7-CH$_3$ | H | —OCH$_3$ | —OCH$_3$ | 194–195 |
| 205 | 7-CH$_3$ | H | —OC$_2$H$_5$ | —OC$_2$H$_5$ | 201–202 |
| 206 | 4-CH$_3$ | H | —OC$_2$H$_5$ | —OC$_2$H$_5$ | 174–175 |
| 207 | 4-CH$_3$ | H | —OCH$_3$ | —OCH$_3$ | 200–201 |
| 208 | 4-CH$_3$ | H | —O-furyl | —O-furyl | 250–251 |
| 209 | 5-CH$_3$ | 7-CH$_3$ | —OCH$_3$ | —OCH$_3$ | 198–199 |
| 210 | 5-CH$_3$ | 7-CH$_3$ | —O-furyl | —O-furyl | 253–255 |
| 211 | 5-CH$_3$ | 7-CH$_3$ | —OC$_2$H$_5$ | —OC$_2$H$_5$ | 218–220 |
| 212 | 7-Cl | H | —OCH$_3$ | —OCH$_3$ | 217–219 |
| 213 | 7-Cl | H | —OC$_2$H$_5$ | —OC$_2$H$_5$ | 212–213 |
| 214 | 7-Cl | H | —O-furyl | —O-furyl | 242–243 |
| 215 | 4-Cl | H | " | " | 242–244 |
| 216 | 6-OCH$_3$ | H | —OCH$_3$ | —OCH$_3$ | 222–223 |
| 217 | 7-O-furyl | H | —OCH$_3$ | —OCH$_3$ | 181–183 |
| 218 | 5-OCH$_2$—CH$_2$—OC$_3$H$_7$ | H | —OCH$_3$ | —OCH$_3$ | 137–138 |
| 219 | 5-SO$_2$C$_2$H$_5$ | H | —OCH$_3$ | —OCH$_3$ | 223–224 |
| 220 | 7-CH—CH$_2$—CH$_3$<br>\|<br>CH$_3$ | H | —OCH$_3$ | —OCH$_3$ | 148–149 |
| 221 | 5-CH$_2$—CH$_2$—CN | H | —OCH$_3$ | —OCH$_3$ | 209–210 |
| 222 | -5-COOCH$_3$ | H | —OCH$_3$ | —OCH$_3$ | 239–241 |
| 223 | -6-OCH$_3$ | 7-CN | —OCH$_3$ | —OCH$_3$ | 302–303 |
| 224 | 4-OCH$_3$ | H | —OCH$_3$ | —OCH$_3$ | 211–212 |
| 225 | 7-furyl | H | —OCH$_3$ | —OCH$_3$ | 226–227 |
| 226 | 6-OCH$_2$—CH$_2$—OC$_2$H$_7$ | H | —OCH$_3$ | —OCH$_3$ | 177–178 |
| 227 | 6-OCH$_2$—CH$_2$—OC$_3$H$_7$ | 7-Cl | —OCH$_3$ | —OCH$_3$ | 178 |
| 228 | 4-CH$_3$ | H | —SC$_2$H$_5$ | —SC$_2$H$_5$ | 192–194 |
| 229 | H | H | —OCH$_3$ | —OCH$_3$ | 222–224 |

The 2-(p-tolyl)-pyrimidines substituted in the 4,6-position, which are required as starting materials for the synthesis of the aldehydes, were prepared in the following way:

102.3 g of p-tolylamidine hydrochloride and 99.3 g of diethyl malonate were suspended in 520 ml of anhydrous ethanol. 323.7 g of a 30% sodium methylate solution are now allowed to run in, with good stirring and cooling. The mixture is then heated to the reflux temperature and refluxed for 4 to 5 hours. After distilling off the solvent, the residue is taken up in 1,000 ml of water, this mixture is heated to 80° C. and the somewhat turbid solution is filtered through silica. After cooling, the filtrate is acidified with 15% hydrochloric acid. The thick crystal slurry is filtered and the crystals are washed with water and dried at 100° C. This yields 100–110 g of the compound of the formula

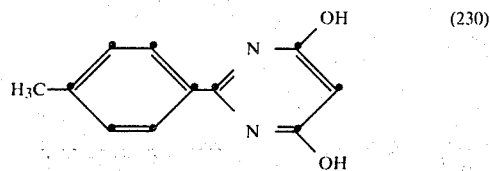
(230)

The product has a melting point of 314° C. (with decomposition).

72.6 g of the dihydroxy compound, 72.6 g of N,N-dimethylaniline and 363 g of phosphorus oxychloride are heated to the boil and the mixture is stirred under reflux for one hour. After distilling off the excess phosphorus oxychloride, the residual product is treated with ice-water, in order to remove the phosphorus oxychloride still adhering thereto, and is then finely ground with ice-water, filtered off, washed with ice-water and dried in vacuo at 40°–50° C. The yield of the compound of the formula

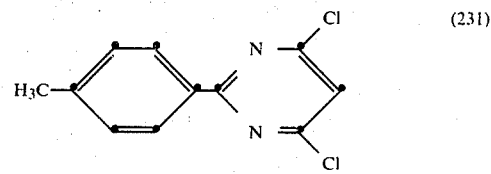
(231)

is 85.9 g. The product has a melting point of 86°–87° C.

156.1 g of a 30.5% sodium methylate solution are stirred with 700 ml of anhydrous methanol. 95.64 g of the compound (231) are now introduced into the solution in the course of 10 minutes, with slight cooling. The mixture is then heated to the reflux temperature and kept at the boil for 4 hours.

After distilling off the solvent, the residual product is introduced into 1,000 ml of water. In order to remove the sodium chloride formed, the product is ground finely with water. It is then filtered off, washed with water and dried in air. This yields 90.4 g of the compound of the formula

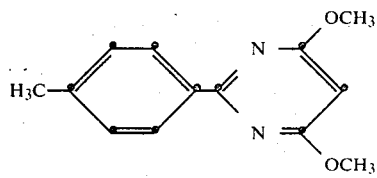

(232)

which has a melting point of 61°–62° C.
The pyrimidines of the formula

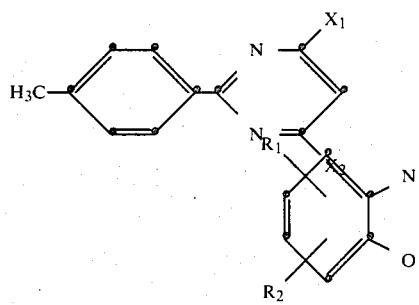

(233)

listed in Table III are prepared analogously:

justed to 7 with acetic acid. The precipitate is filtered off with suction, washed with water and dried. After repeated recrystallisation from toluene/ligroin (1:1), with the aid of bleaching earth, 10.6 g, corresponding to 82% of theory, of the compound of the formula

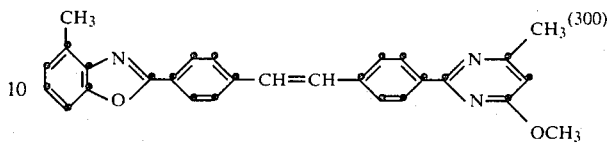

(300)

are obtained in the form of a yellowish powder with a melting point of 187°–188° C.
The compounds of the formula

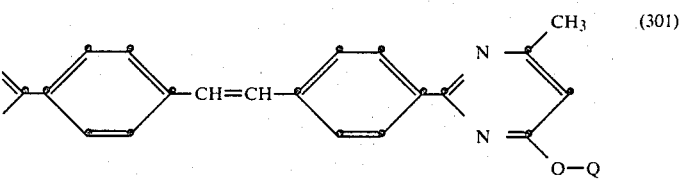

(301)

listed in Table (IV) are prepared analogously from the corresponding starting materials.

TABLE III

| Compound No. | $X_1$ | $X_2$ | Melting point °C. |
|---|---|---|---|
| 234 | —OC$_2$H$_5$ | —OC$_2$H$_5$ | 70–71 |
| 235 | —OCH(CH$_3$)$_2$ | —OCH(CH$_3$)$_2$ | yellowish oil |
| 236 | —O—C$_6$H$_5$ | —O—C$_6$H$_5$ | 125–126 |
| 237 | —OCH$_2$—CH$_2$—OCH$_3$ | —OCH$_2$—CH$_2$—OCH$_3$ | pale yellow oil |
| 238 | morpholino | morpholino | 186–187 |
| 239 | —NH—CH$_3$ | —OCH$_2$—CH$_2$—OCH$_3$ | 65–66 |
| 240 | —N(C$_2$H$_5$)$_2$ | —OCH$_2$—CH$_2$—OCH$_3$ | pale yellow oil |
| 241 | —NH—CH$_3$ | Cl | 107 |
| 242 | —N(C$_2$H$_5$)$_2$ | Cl | 74–75 |
| 243 | —OC$_3$H$_7$ | —OC$_3$H$_7$ | 62 |
| 244 | —SC$_2$H$_5$ | —SC$_2$H$_5$ | 55–56 |

TABLE IV

| Compound No. | $R_1$ | $R_2$ | Q | Melting point °C. |
|---|---|---|---|---|
| 302 | 7-CH$_3$ | H | CH$_3$ | 178–179 |
| 303 | 7-Cl | H | CH$_3$ | 192–193 |
| 304 | 7-CH(CH$_3$)$_2$ | H | C$_6$H$_5$ | 191–192 |
| 305 | 7-Cl | H | C$_6$H$_5$ | 227–228 |
| 306 | 7-CH$_3$ | 5-CH$_3$ | C$_6$H$_5$ | 200–201 |

EXAMPLE 3:

2.1 g of solid sodium methylate are introduced in portions, in the course of 15 minutes, at 40° C., into a solution of 6.85 g of 2-(4-diethoxy-phosphorylmethyl-phenyl)-4-methylbenzoxazole and 10.8 g of 2-(4-formyl-phenyl)-4-methyl-6-methoxy-pyrimidine in 100 ml of dimethylformamide. The reaction mixture is then stirred at 45° C. for 3 hours and poured into 1,000 ml of ice-water and the pH of the aqueous suspension is ad-

TABLE IV-continued

| Compound No. | R₁ | R₂ | Q | Melting point °C. |
|---|---|---|---|---|
| 307 | 4-CH₃ | H | C₆H₅ | 234-235 |

The aldehyde used, which has the formula

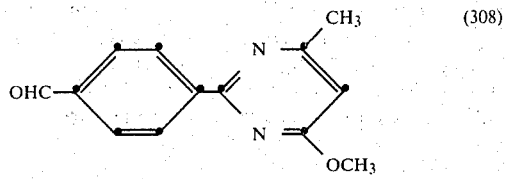
(308)

is obtained as follows:

A solution of 54 g of sodium methylate in 130 ml of methanol is added dropwise, at 60° C., to a solution of 85 g of p-tolylamidine hydrochloride and 80.5 g of ethyl acetoacetate in 250 ml of methanol. The reaction mixture is then kept under reflux for 4 hours and poured into 1,000 ml of water and the pH is adjusted to 6 to 7 with acetic acid. The precipitate is filtered off with suction, washed with water and dried. This yields 94.4 g (94% of theory) of 4-hydroxy-6-methyl-2-p-tolyl-pyrimidine with a melting point of 206°-207° C.

4-Hydroxy-6-phenyl-2-p-tolylpyrimidine with a melting point of 282°-283° C. is obtained when the same procedure is repeated except that equivalent amounts of ethyl benzoylacetate are used in place of the 80.5 g of ethyl acetoacetate.

183 g of phosphorus oxychloride are initially introduced at 5° C. and 20 g of triethylamine are added dropwise at this temperature. 80 g of 4-hydroxy-6-methyl-2-p-tolylpyrimidine are introduced into this mixture at 10°-15° C. The reaction mixture is then heated to 100° C. in the course of 30 minutes, stirred at this temperature for 1 hour, cooled and poured into ice-water. After filtering off the product with suction, washing until neutral and drying, this yields 85.5 g (98% of theory) of 4-chloro-6-methyl-2-p-tolylpyrimidine with a melting point of 103°-104° C.

4-Chloro-6-phenyl-2-p-tolylpyrimidine with a melting point of 86°-87° C. is obtained when the same procedure is repeated except that equivalent amounts of 4-hydroxy-6-phenyl-2-p-tolylpyrimidine are used in place of the 80 g of 4-hydroxy-6-methyl-2-p-tolylpyrimidine.

A solution of 11.5 g of sodium in 100 ml of methanol is introduced into a suspension of 76.5 g of 4-chloro-6-methyl-2-p-tolylpyrimidine in 200 ml of methanol and the reaction mixture is refluxed for 2 hours and poured into water. After filtering off the product with suction, washing with water and drying, this yields 72.9 g (97% of theory) of 4-methoxy-6-methyl-2-p-tolylpyrimidine with a melting point of 66°-67° C.

4-Methoxy-6-phenyl-2-p-tolylpyrimidine with a melting point of 99°-100° C. is obtained when the same procedure is repeated except that equivalent amounts of 4-chloro-6-phenyl-2-p-tolylpyrimidine are used in place of the 76 g of 4-chloro-6-methyl-2-p-tolylpyrimidine.

A mixture of 9.4 g of N-bromosuccinimide and 0.2 g of azoisobutyronitrile is added in portions, in the course of 30 minutes, at 70° C. to a solution of 10.7 g of 4-methoxy-6-methyl-2-p-tolylpyrimidine and 0.2 g of dibenzoyl peroxide in 100 ml of anhydrous carbon tetrachloride and the mixture is then refluxed for 2 hours. After cooling, the succinimide is filtered off with suction, the material on the suction filter is washed with 200 ml of carbon tetrachloride and the filtrate is evaporated. After recrystallising the residue from n-hexane, this yields 11 g (75% of theory) of 2-(4-bromomethyl-phenyl)-4-methoxy-6-methylpyrimidine with a melting point of 98°-99° C.

2-(4-Bromomethylphenyl)-4-methoxy-6-phenyl-pyrimidine with a melting point of 98°-100° C. is obtained when the same procedure is repeated except that an equivalent amount of 4-methoxy-6-phenyl-2-p-tolyl-pyrimidine is used in place of the 10.7 g of 4-methoxy-6-methyl-2-p-tolylpyrimidine.

23.2 g of nitropropane are introduced into a solution of 5 g of sodium in 400 ml of ethanol at 20°-25° C. After stirring for 30 minutes, 60.4 g of 2-(4-bromomethyl-phenyl)-4-methoxy-6-methylpyrimidine in 100 ml of dimethylformamide are added and the reaction mixture is then refluxed for 4 hours. After cooling, the product is filtered off with suction and the filter cake is washed with ethanol and dried. After recrystallising from ethanol, this yields 15.6 g (32% of theory) of 2-(4-formyl-phenyl)-4-methoxy-6-methylpyrimidine [formula (308)] with a melting point of 125°-126° C.

The aldehyde of the formula

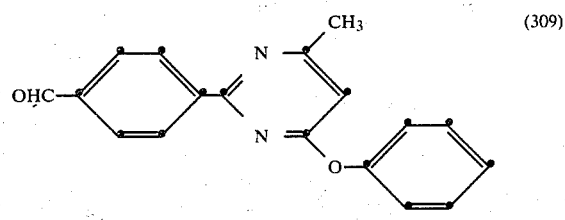
(309)

is also prepared analogously. Yield 43 g (59.5% of theory), melting point 99°-101° C.

The 2-p-tolyl-4-methyl-6-phenoxypyrimidine required for this reaction is prepared as follows:

A mixture consisting of 250 g of phenol and 29.7 g of sodium methylate is heated, whilst at the same time distilling off the methanol formed until an internal temperature of 160° C. is reached. The melt is then cooled to 120° C., 109 g of 4-chloro-6-methyl-2-p-tolylpyrimidine are added and the mixture is stirred at 120° C. for 3 hours. After cooling, the excess phenol is removed with steam, the residue is filtered with suction and the product is washed with water and dried. After recrystallisation from methanol, this yields 119.4 g (86.5% of theory) of 4-methyl-6-phenoxy-2-p-tolylpyrimidine with a melting point of 90°-91° C.

2-(4-Bromomethylphenyl)-4-methyl-6-phenoxypyrimidine is prepared as described above using N-bromosuccinimide and is obtained in 76% yield; the product has a melting point of 126°-127° C.

EXAMPLE 4

2.1 g of solid sodium methylate are introduced in portions, in the course of 15 minutes, at 40° C., into a solution of 7.1 g of 2-(4-formylphenyl)-4-methylbenzoxazole and 12.4 g of 2-(4-diethoxyphosphorylmethyl-phenyl)-4-methoxy-phenyl-pyrimidine in 100 ml of dimethylformamide. The reaction mixture is then stirred at 45° C. for 3 hours and poured into 1,000 ml of ice-water and the pH of the aqueous suspension is adjusted to 7 with acetic acid. The precipitate is filtered off with suction, washed with water and methanol and dried. After repeated recrystallisation from toluene/n-hexane (1:1), with the aid of bleaching earth, 8.8 g, corresponding to 59% of theory, of the compound of the formula

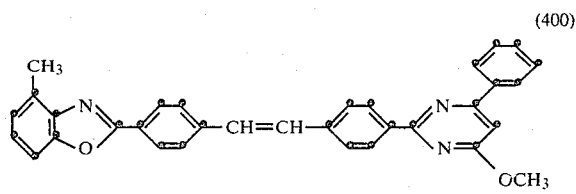

are obtained in the form of a yellowish powder with a melting point of 200°–201° C.

The compounds of the formula

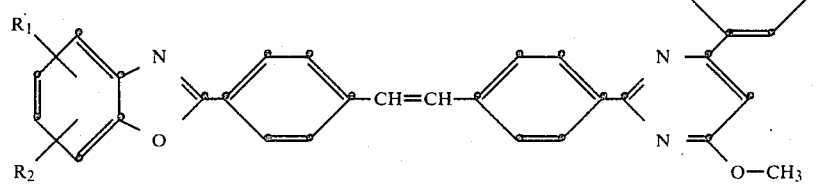

listed in Table (V) are prepared in an analogous manner from the corresponding starting materials.

TABLE (V)

| Compound No. | $R_1$ | $R_2$ | Melting point °C. |
|---|---|---|---|
| 402 | 7-CH$_3$ | H | 188–189 |
| 403 | 7-Cl | H | 21–215 |
| 404 | 5-CH$_3$ | 7-CH$_3$ | 222–223 |

The diethoxyphosphorylmethyl compound of the formula

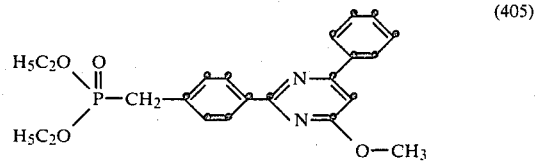

which is used is prepared in the following way:

A mixture consisting of 89 g of 2-(4-bromomethylphenyl)-4-methoxy-6-phenylpyrimidine and 166 g of triethyl phosphite is warmed slowly to 150° C., with stirring, and is then stirred at this temperature for 5 hours. The bulk of the excess triethyl phosphite is then distilled off in vacuo and the residue is subjected to chromatography on silica gel. Yield 79.3 g (77% of theory) in the form of colourless crystals with a melting point of 73°–75° C.

EXAMPLE 5

2.1 g of sodium methylate are added in the course of 20 minutes, at 45° C., to a solution of 11.2 g of 2-(4-diethoxyphosphorylmethylphenyl)-7-ethyl-benzoxazole and 6.85 g of 2-methyl-4-methoxy-6-(4-formylphenyl)-pyrimidine in 100 ml of dimethylformamide. The reaction mixture is stirred for a further 3 hours at 40°–45° C. and introduced into 800 ml of ice-water and the resulting mixture is rendered slightly acid with formic acid. The product which has precipitated is filtered off, washed with water and methanol and dried in vacuo at 80° C. 12.2 g of the crude product of the formula

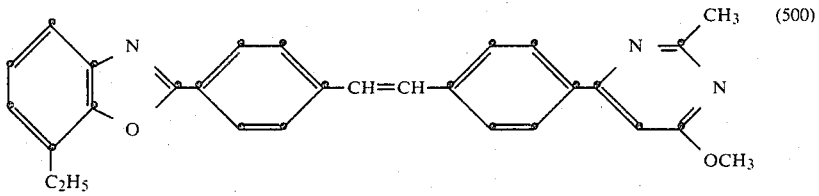

are obtained. After recrystallisation from benzene/cyclohexane (1:1) in the presence of bleaching earth, the crystalline product has a melting point of 183°–184° C.

The aldehyde used, which has the formula

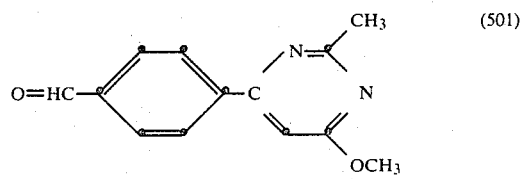

is prepared in the following way:

70.9 g of acetamidine hydrochloride and 154.65 g of ethyl p-tolylacetate in 450 ml of anhydrous methanol are heated to 60° C. 265.6 g of a 30.5% sodium methylate solution are now allowed to run in at this temperature, in the course of one hour. The resulting suspension is refluxed for a further 3 hours. After cooling, the reaction mixture is stirred into 1,500 ml of ice and water and a yellow solution forms. After acidifying with 45 ml of glacial acetic acid, a thick, colourless crystal slurry forms. This is filtered and the crystals are washed with water until acid-free and dried at 70°–80° C. in vacuo. 95 g of the crude product of the formula

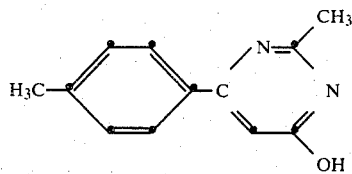
(502)

are obtained. The compound can be purified by recrystallisation from chlorobenzene (melting point 278°–279° C.).

76 g of the 2-methyl-4-hydroxy-6-(p-tolyl)-pyrimidine are introduced in the course of 10 minutes into a mixture consisting of 171 g of phosphorus oxychloride and 19 g of triethylamine, with cooling and good stirring. A thick slurry forms and this is now heated to 100°–105° C. in the course of 30 minutes, whereupon a solution forms, which is stirred for a further one hour at 100°–105° C. After cooling to 50° C., the reaction solution is allowed to run into a mixture of 1,000 ml of water and ice, with rapid stirring. The product which has precipitated is stirred ice-cold for a further 20 minutes and is then filtered off, washed with ice-cold water and dried in air. 86.5 g of the crude product of the formula

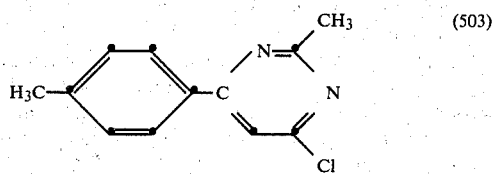
(503)

are obtained. The product is purified by dissolving in 400 ml of hexane, filtering off a small amount of undissolved brown by-product and evaporating the yellow hexane solution in vacuo. A yellow oil is obtained and on cooling this solidifies to give pale yellow crystals. Yield 81 g.

76.51 g of the crude product are introduced, without further purification, into 350 ml of anhydrous methanol containing 69.3 g of a 30% sodium methylate solution and the resulting mixture is heated to the reflux temperature and refluxed for 4 hours. The reaction mixture is then evaporated to dryness, the resulting crystal slurry is treated with 1,000 ml of ice-water and the product is filtered off, washed with water and dried in vacuo at 40°–50° C. 75.1 g of the crude product of the formula

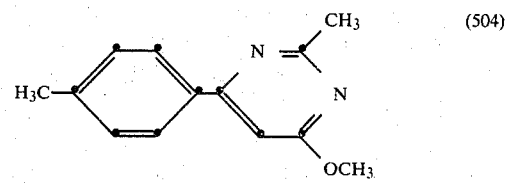
(504)

are obtained. The product crystallises from methanol in the form of colourless crystals with a melting point of 78°–79° C.

Using the procedure described under Example 1, the product is now brominated in the side chain with N-bromosuccinimide (melting point of 2-methyl-4-methoxy-6-(4-bromomethylphenyl)-pyrimidine 93°–94° C.) and then oxidised with 2-nitropropane to give 2-methyl-4-methoxy-6-(4-formylphenyl)-pyrimidine of the formula

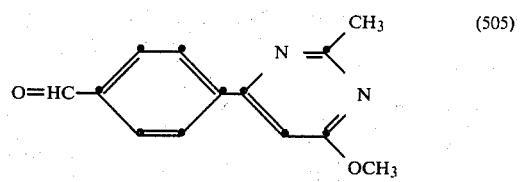
(505)

(melting point 114°–115° C.).

EXAMPLE 6

11.83 g of 2-methyl-4-methoxyethoxy-6-(4-diethoxyphosphorylmethylphenyl)-pyrimidine and 7.54 g of 2-(4-formylphenyl)-5,7-dimethyl-benzoxazole are dissolved in 100 ml of dimethylformamide and 2.1 g of sodium methylate are added in the course of 10 minutes at 45° C., with stirring. The reaction mixture is stirred at 40°–45° C. for a further 2½ hours and is then cooled and stirred into 800 ml of ice-water. The mixture is acidified with formic acid and the product which has precipitated is filtered off, washed with water and methanol and dried in vacuo at 60°–70° C. 12.4 g of the crude product of the formula

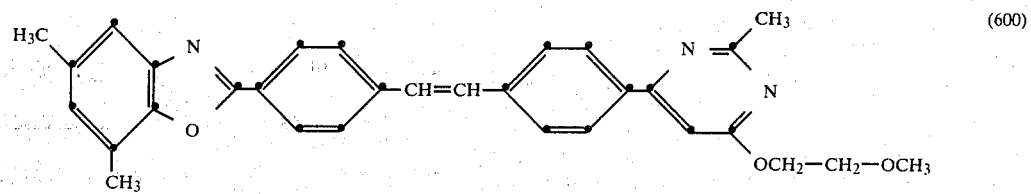
(600)

are obtained. After recrystallising from a 1:1 mixture of benzene/cyclohexane in the presence of bleaching earth, pale greenish-tinged yellow crystals with a melting point of 156°–158° C. are obtained.

The phosphonate of the formula

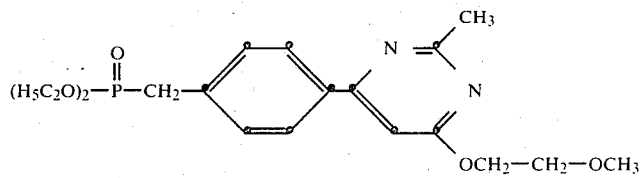
(601)

which is required for the synthesis, is prepared in the following way:

85.3 g of 2-methyl-4-chloro-6-(4-methylphenyl)-pyrimidine are introduced into a solution of 9.9 g of sodium in 300 ml of dry ethylene glycol monomethyl ether, with stirring and ice-cooling. The mixture is then heated to the reflux temperature and stirred under reflux for 3 hours. The excess ethylene glycol monomethyl ether is then distilled off and the somewhat dark oil obtained is taken up in chloroform. The chloroform solution is twice extracted by shaking with, in each case, 500 ml of water and is then dried over anhydrous sodium sulfate and evaporated to dryness. 94.2 g of the crude product of the formula

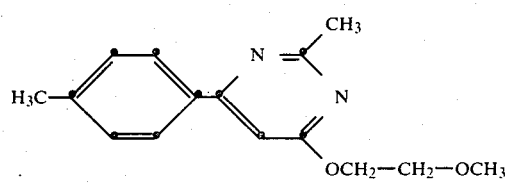
(602)

are obtained in the form of an oil, which solidifies to crystals overnight. Melting point of the compound 61°–62° C.

Using the procedure described in Example 1, 91.7 g of 2-methyl-4-methoxy-ethoxy-6-(4-methylphenyl)-pyrimidine are brominated in the side chain with N-bromosuccinimide in carbon tetrachloride. 114 g of 2-methyl-4-methoxyethoxy-6-(4-bromomethylphenyl)-pyrimidine of the formula

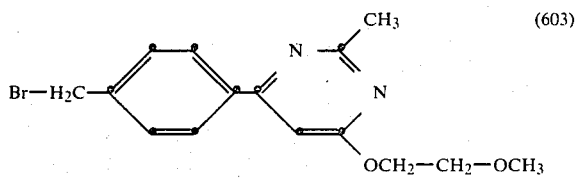
(603)

are obtained in the form of a pale yellow oil, which is further processed without further purification.

111.3 g of 2-methyl-4-methoxyethoxy-6-(4-bromomethyl-phenyl)-pyrimidine and 320 ml of triethyl phosphite are heated to 150°–155° C. in the course of 1½ hours. The mixture is then stirred at this temperature for a further 2 hours. After distilling off the excess triethyl phosphite, 126.2 g of the compound of the formula

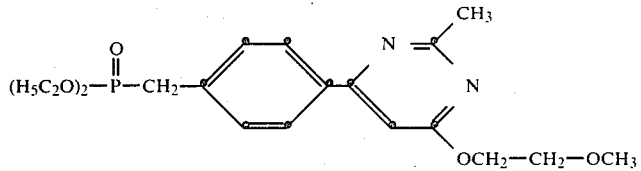
(604)

are obtained in the form of a brown oil. The compound was purified by column chromatography on silica gel.

Solvents and solvent system: toluene/methanol in a ratio of 9:1. 119.4 g of the phosphonate were obtained in the form of a pale yellow, viscous oil.

2-(4-Formylphenyl)-5,7-dimethyl-benzoxazole of the formula

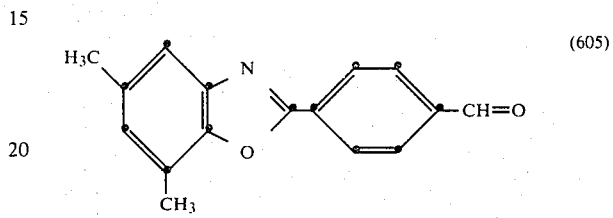
(605)

was prepared in the following way.

46.32 g of 2-nitropropane are allowed to run, at room temperature, into a solution of 9.2 g of sodium in 600 ml of anhydrous ethanol. After stirring for 3 hours at room temperature, 108.7 g of 2-(4-chloromethylphenyl)-5,7-dimethyl-benzoxazole (prepared by a condensation reaction of 4,6-dimethyl-2-aminophenol with 4-chloromethyl-benzoyl chloride and subsequent cyclisation in o-dichlorobenzene in the presence of p-toluenesulphonic acid: melting point 118°–119° C.) and 150 ml of dimethylformamide are added. The reaction mixture is heated to 60°–65° C., whereupon a solution forms. After stirring for 1½ hours at 60°–65° C., the solution is allowed to cool to room temperature in the course of 14 hours. The product which has precipitated is filtered off at 5° C., washed with ethanol and dried in vacuo at 70° C. The yield is 74.5 g. Melting point: 155°–157° C. A further 16.6 g of less pure product can be obtained from the filtrate, by precipitating with water.

The aldehydes of the formula

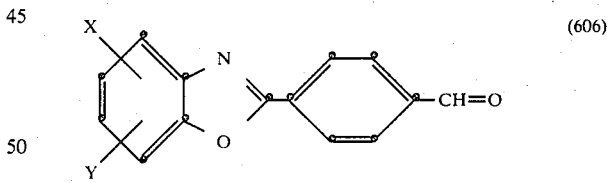
(606)

listed in Table IV are obtained analogously.

TABLE VI

| Compound No. | X | Y | Melting point °C. |
|---|---|---|---|
| 607 | 4-CH₃ | H | 187–189 |

TABLE VI-continued

| Compound No. | X | Y | Melting point °C. |
|---|---|---|---|
| 608 | 7-CH$_3$ | H | 142–143 |
| 609 | 7-Cl | H | 189–190 |
| 610 | 6-Cl | 7-Cl | 191–192 |

EXAMPLE 7

The compounds of the formula

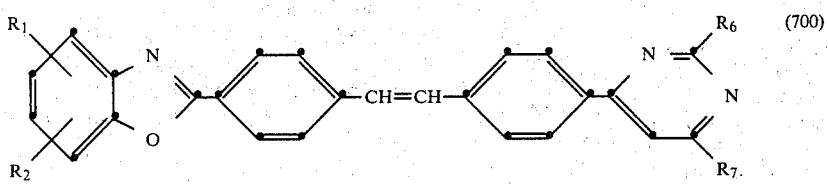

listed in Table (VII) are obtained by the procedure described in Example 5 or 6.

TABLE VII

| Compound No. | R$_1$ | R$_2$ | R$_6$ | R$_7$ | Melting point °C. |
|---|---|---|---|---|---|
| 701 | 4-CH$_3$ | H | —CH$_3$ | —OCH$_3$ | 227–228 |
| 702 | 7-Cl | H | —CH$_3$ | —OCH$_3$ | 247–249 |
| 703 | 4-Cl | H | —CH$_3$ | —OCH$_3$ | 249–250 |
| 704 | 5-CH$_3$ | 7-CH$_3$ | —CH$_3$ | —OCH$_3$ | 224–225 |
| 705 | 7-CH$_3$ | H | —CH$_3$ | —OCH$_2$—CH$_2$—OCH$_3$ | 162–163 |
| 706 | 7-Cl | H | —CH$_3$ | —O—CH$_2$—CH$_2$—OCH$_3$ | 177–178 |

EXAMPLE 8

8.79 g of 5,7-dimethyl-2-(4-formylphenyl)-benzoxazole and 11.70 g of 2-(4-diethoxyphosphorylmethyl-phenyl)-4,6-dimethyl-pyrimidine are dissolved in 120 ml of dimethylformamide and the solution is heated to 40°–45° C. 2.5 g of sodium methylate are now stirred into the resulting solution in the course of 20 minutes, with slight cooling. The reaction mixture is stirred at this temperature for a further 2½ hours and is then cooled to room temperature, acidified with formic acid and then stirred into 800 ml of water. The product which has precipitated is filtered off, washed with water and with methanol and dried. 12.7 g of the compound of the formula

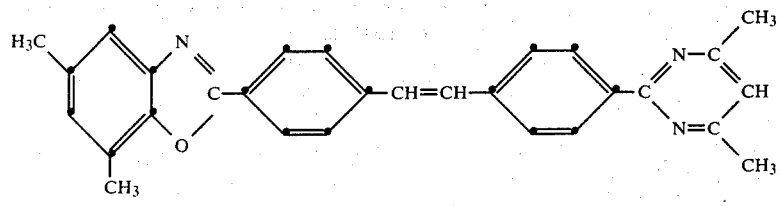

are obtained. The product crystallises from toluene, with the addition of bleaching earth, in the form of yellow crystals with a melting point of 239°–240° C.

The 2-(4-diethoxyphosphorylmethyl-phenyl)-4,6-dimethyl-pyrimidine (melting point 67°–69° C.) required as the starting material for the synthesis is obtained by brominating 2-p-tolyl-4,6-dimethyl-pyrimidine in the side chain and reacting the resulting 2-(4-bromomethylphenyl)-4,6-dimethyl-pyrimidine (melting point 156°–157° C.) with triethyl phosphite at 140°–145° C.

The following phosphonates of the formula

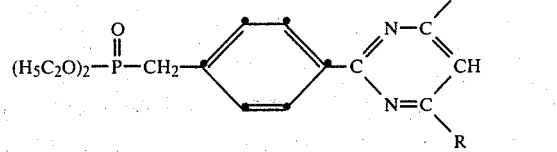

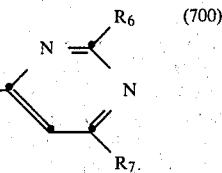

| Compound No. | R | Melting point or boiling point °C. |
|---|---|---|
| 802 | —OCH$_3$ | Boiling point$_{13.332\ Pa}$ 208–210 |
| 803 | —OC$_2$H$_5$ | Pale yellow oil |
| 804 | —OC$_3$H$_7$ | 77–79 |
| 805 | —O—⟨furyl⟩ | Colourless, semi-solid product |
| 806 | —SC$_2$H$_5$ | pale yellow oil | and also the phosphonates of the formula

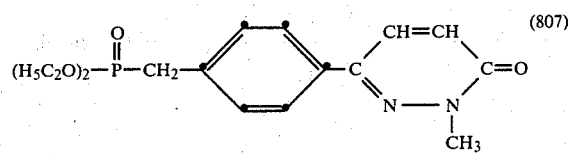

with a melting point of 91°–92° C., and

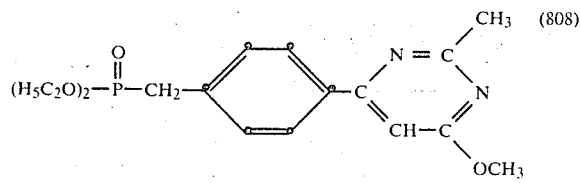 (808)

with a melting point of 82°–83° C., are also obtained by the same reaction procedure.

EXAMPLE 9

8.3 g of 4-methyl-2-(4-formylphenyl)-benzoxazole and 10.72 g of 2-(4-diethoxy-phosphorylmethylphenyl)-pyrimidine are heated with 140 ml of dimethylformamide to 40° C. 2.5 g of solid sodium methylate are now introduced in the course of 20 minutes at 40°–45° C., with slight cooling. The reaction mixture is then stirred at 40°–45° C. for a further 3 hours. After cooling to room temperature, the mixture is acidified with formic acid and introduced into 800 ml of water and ice. The product which has precipitated is filtered off, washed with water and methanol and dried in vacuo. 11.9 g of the compound of the formula

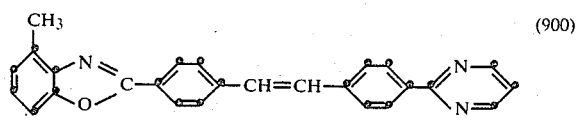 (900)

are obtained. The product crystallises from xylene, in the presence of bleaching earth, in the form of pale green-yellow crystals with a melting point of 241°–242° C.

The 2-(4-diethoxy-phosphorylmethylphenyl)-pyrimidine required for the synthesis is prepared in the following way:

95.64 g of 2-p-tolyl-4,6-dichloropyrimidine of the formula (231) are hydrogenated in 1,800 ml of anhydrous ethanol, with the addition of 72.2 g of anhydrous sodium acetate and 10 g of 5% Pd/C, with hydrogen at room temperature. After filtering off the catalyst, the ethanolic solution is evaporated to dryness and the solid product obtained is treated with water. After drying, 61.9 g of the compound of the formula

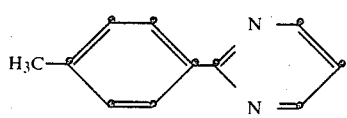 (901)

are obtained in the form of colourless crystals with a melting point of 88°–89° C.

Using the procedure described in Example 1, 61.3 g of 2-p-tolyl-pyrimidine are brominated in the side chain with N-bromosuccinimide. 90.3 g of the compound of the formula

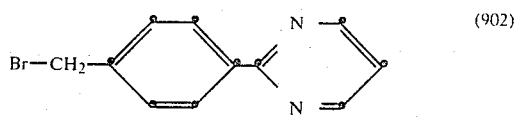 (902)

are obtained and this compound crystallises from methanol in the form of colourless crystals with a melting point of 103°–104° C.

88.3 g of 2-(4-bromomethylphenyl)-pyrimidine of the formula (902) and 350 ml of triethyl phosphite are heated to 145°–150° C. and the mixture is stirred for 4 hours at this temperature. After distilling off the excess triethyl phosphite in vacuo, 108 g of the compound of the formula

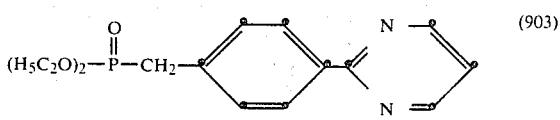 (903)

are obtained in the form of a pale yellow oil, which solidifies to crystals after a few days.

EXAMPLE 10

3.5 g of solid sodium methylate are introduced in portions, in the course of 15 minutes, at 40° C., into a solution of 16 g of 2-(4-diethoxy-phosphorylmethylphenyl)-4-methyl-pyridine and 11.9 g of 2-(4-formylphenyl)-4-methylbenzoxazole in 170 ml of dimethylformamide. The reaction mixture is then stirred at 45° C. for 5 hours and poured into 700 ml of ice-water and the pH of the aqueous suspension is adjusted to 7 with acetic acid. The precipitate is filtered off with suction, washed with water and dried. After repeated recrystallisation from toluene/ligroin (1:1), with the aid of bleaching earth, 11.8 g, corresponding to 59% of theory, of the compound of the formula

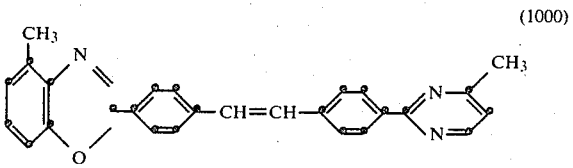 (1000)

are obtained in the form of a yellowish product with a melting point of 220°–221° C.

The compounds of the formula

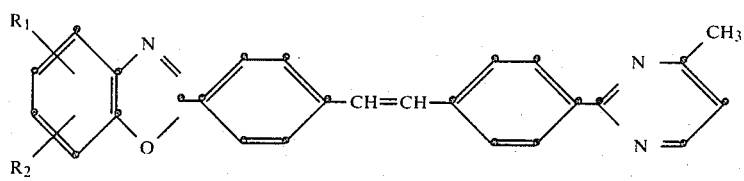

listed in Table VIII are prepared analogously from the corresponding starting materials.

TABLE VIII

| Compound No. | R₁ | R₂ | Melting point °C. |
|---|---|---|---|
| 1001 | 7-CH₃ | H | 207–208 |
| 1002 | 7-CH₃ | 5-CH₃ | 203–204 |
| 1003 | 7-Cl | H | 237–238 |

The phosphonate used, which has the formula

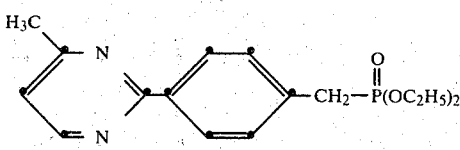

is obtained as follows:

A solution of 108 g of sodium methylate in 260 ml of methanol is added dropwise at 50° C. to a solution of 170 g of p-tolylamidine hydrochloride and 150 g of 1-acetyl-2,2-dimethoxyethane in 500 ml of methanol. The reaction mixture is then stirred at 50° C. for 4 hours and poured into 2,000 ml of water and the pH of the resulting mixture is adjusted to 7 with acetic acid. The precipitate is filtered off with suction, washed with water and dried. This yields 167 g (91% of theory) of 2-(4-methylphenyl)-4-methyl-pyrimidine with a melting point of 80°–81° C.

This 2-(4-methylphenyl)-4-methyl-pyrimidine is reacted with N-bromosuccinimide in the manner described in Example 3, yielding, after recrystallisation from ligroin, 2-(4-bromomethylphenyl)-4-methyl-pyrimidine with a melting point of 104°–106° C.

A mixture consisting of 105 g of 2-(4-bromomethylphenyl)-4-methyl-pyrimidine and 265 g of triethyl phosphite is warmed slowly to 150° C., with stirring and whilst at the same time distilling off the ethyl bromide formed, and is then stirred for 5 hours at this temperature. After distilling off the excess triethyl phosphite, 125 g of the phosphonate are obtained in the form of a pale brown, viscous oil.

EXAMPLE 11

3.82 g of the Schiff's base of the formula

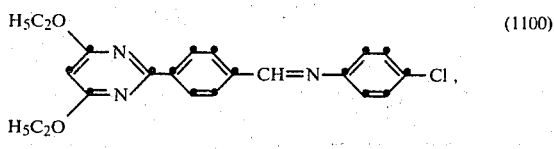
(1100)

which is obtained from 4,6-diethoxy-2-(p-formylphenyl)-pyrimidine and p-chloroaniline and has a melting point of 129.5°–130° C., 2.23 g of 5-methyl-2-(p-tolyl)-benzoxazole of the formula

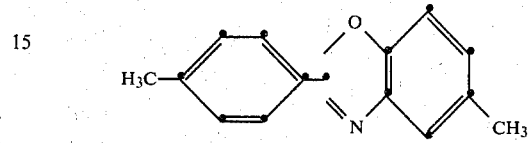

and 3.75 g of potassium hydroxide powder with a water content of about 10% are stirred in 80 ml of dimethylformamide under nitrogen. The reaction mixture is warmed to 60° C. in the course of 15 minutes and is stirred for a further one hour at 60°–65° C. After adding 400 ml of methanol, the mixture is cooled to −10° C. and the product which has precipitated is filtered off with suction, washed with 100 ml of methanol and dried. 2.64 g (55.3% of theory) of 2-[4'-(5-methyl-benzoxazol-2-yl)-stilben-4-yl]-4,6-diethoxy-pyrimidine of the formula

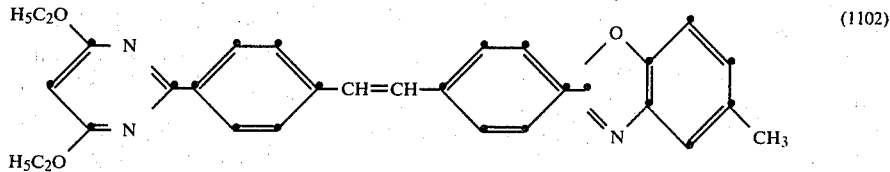
(1102)

are obtained in the form of a pale yellow powder with a melting point of 233°–234° C. After twice recrystallising from toluene, and with the aid of bleaching earth, 2.12 g (44.4% of theory) of small, pale greenish-tinged yellow, matted needles are obtained, which melt at 236°–237° C.

The compounds of the formula

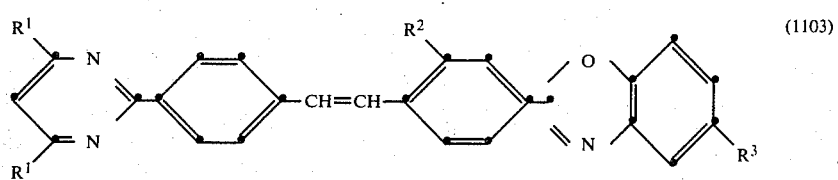
(1103)

listed in Table IX below, can be prepared analogously:

TABLE IX

| Compound No. | R¹ | R² | R³ | Melting point °C. | Reaction temperature °C. |
|---|---|---|---|---|---|
| 1104 | CH₃O | H | H | 222–223 | 60–65 |
| 1105 | CH₃O | H | CH₃ | 239–240 | 60–65 |
| 1106 | CH₃O | H | CH₃O | 219–220 | 60–65 |
| 1107 | CH₃O | H | C₆H₅ | 241–242 | 60–65 |
| 1108 | C₂H₅O | H | H | 242–243 | 60–65 |
| 1109 | C₂H₅O | H | CH₃O | 219–220 | 60–65 |
| 1110 | CH₃O | Cl | H | 226–227 | 40–45 |

TABLE IX-continued

| Compound No. | | | | Melting point °C. | Reaction temperature °C. |
|---|---|---|---|---|---|
| 1111 | CH$_3$O | Cl | t-C$_4$H$_9$ | 191–192 | 40–45 |
| 1112 | CH$_3$O | Cl | H | 216–217 | 40–45 |

EXAMPLE 12

Using a liquor ratio of 1:20, a polyester fabric (Terylene type 540) is treated on a dyeing apparatus with an aqueous bath which contains 0.1% (based on the weight of goods) of the compound of the formula (100), (109), (112), (300), (704), (800), (1000) or (1002) and 1 g/liter of the condensation product of 35 mols of ethylene oxide and 1 mol of stearyl alcohol. The bath is now warmed from 40° to 120° C. in the course of 30 minutes, is kept at this temperature for 30 minutes and is then cooled to 15° C. in the course of 15 minutes. The fabric is then rinsed in running deionised water and dried at 70° C. The polyester fabric treated in this way displays a good white effect.

EXAMPLE 13

A polyester fabric (Terylene type 540) is padded at room temperature with a liquor which contains, per liter, 1 g of the compound of the formula (200), (206), (218), (302), (706) or (800) and 1 ml of the condensation product of 8–9 mols of ethylene oxide and 1 mol of p-tert.-octylphenol. The liquor pick-up is 80%. The fabric is then dried for 10 minutes at 80° C. and is then subjected to thermofixing at 200° C. for 30 seconds. The fabric treated in this way displays a good white effect.

EXAMPLE 14

Using a liquor ratio of 1:20, a polyester/cotton mixed fabric is treated on a dyeing apparatus with an aqueous bath which contains 0.1% based on the weight of goods, of the compound of the formula (108), (109), (111), (218) or (300) and 1 g/liter of the condensation product of 35 mols of ethylene oxide and 1 mol of stearyl alcohol. The bath is now warmed from 40° to 97° C. in the course of 30 minutes, kept at this temperature for 30 minutes and then cooled to 15° C. in the course of 15 minutes. The fabric is then rinsed in running deionised water and dried at 70° C. The polyester/cotton mixed fabric treated in this way is distinguished by a good white effect.

EXAMPLE 15

Using a liquor ratio of 1:20, a polyamide-6,6 woven tricot is treated on a dyeing apparatus with an aqueous bath which contains 0.2%, based on the weight of goods, of the compound (105), (106), (218), (303) or (702) and 3 g/liter of a mixture of 60 parts by weight of sodium hydrosulfite and 40 parts by weight of sodium pyrophosphate. The bath is warmed from 40° to 130° C. in the course of 30 minutes, kept at this temperature for 30 minutes and then cooled to 15° C. in the course of 15 minutes. The fabric is then rinsed in running deinoised water and dried at 60° C. The polyamide fabric treated in this way displays a good white effect.

EXAMPLE 16

Using a liquor ratio of 1:20, a triacetate fabric is treated on a dyeing apparatus with an aqueous bath which contains 0.1%, based on the weight of goods, of the compound of the formula (109), (302), (303), (600) or (701) and 1 g/liter of the condensation product of 35 mols of ethylene oxide and 1 mol of stearyl alcohol. The bath is now warmed from 40° to 97° C. in the course of 30 minutes, kept at this temperature for 30 minutes and then cooled to 30° C. in the course of 15 minutes. The fabric is then rinsed in running deionised water and dried at 60° C. The triacetate fabric treated in this way displays a good white effect.

EXAMPLE 17

Using a liquor ratio of 1:20, an acetate satin fabric is treated on a dyeing apparatus with an aqueous bath which contains 0.1%, based on the weight of goods, of the compound of the formula (106), (110), (220), (221) or (600), 1 g/liter of the condensation product of 35 mols of ethylene oxide and 1 mol of stearyl alcohol and 0.5 ml/liter of 80% acetic acid. The bath is now warmed from 40° to 80° C. in the course of 30 minutes, kept at this temperature for 30 minutes and then cooled to 20° C. in the course of 15 minutes. The fabric is then rinsed in running deionised water and dried at 60° C. The acetate satin fabric treated in this way is distinguished by a good white effect.

EXAMPLE 18

1,000 g of polyester granules of the ethylene glycol terephthalate type, containing 0.5% of TiO$_2$ (anatase type), are mixed with 0.5 g of a compound of the formula (214), (215), (306) or (307) in a rotary wheel mixer, and the granules treated in this way are spun in an extruder spinning installation at 280° C. to give a multifilament. The resulting filaments display an excellent white effect with good fastness to light.

EXAMPLE 19

100 parts of polystyrene, containing about 1.5% of TiO$_2$ (rutile type), and 0.05 part of a compound of the formula (209), (210), (215), (304) or (307 are mixed in the form of the dry compounds and the mixture is processed on an extruder at 180° C. to give whitened granules. The granules are moulded to small sheets with the aid of a piston injection moulding machine. The small sheets thus obtained display a powerful white effect with good fastness to light.

EXAMPLE 20

An intimate mixture of 65 parts of polyvinyl chloride (suspension type), 32 parts of dioctyl phthalate, 3 parts of an epoxidised soya bean oil, 1.5 parts of a stabiliser, 0.5 part of a co-stabiliser, 5 parts of TiO$_2$ (rutile type) and 0.05 part of a compound of the formula (208), (400), (402), (403) or (404) is rolled out on a calender at 150° C. to give a film. The resulting film displays a powerful white effect with good fastness to light.

What is claimed is:

1. A benzoxazolyl-stilbene of the formula

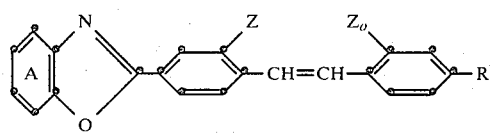

in which R is one of the ring systems of the formulae

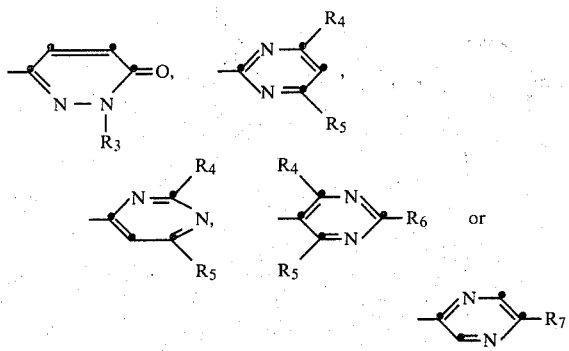

in which $R_3$ is hydrogen, alkyl having 1 to 4 C atoms, unsubstituted phenyl or phenyl substituted by chlorine or methyl, $R_4$ and $R_5$ independently of one another are hydrogen, alkyl having 1 to 4 C atoms, unsubstituted phenyl or phenyl substituted by chlorine or methyl, alkoxy having 1 to 4 C atoms, alkoxyalkoxy having a total of 3 to 8 C atoms, unsubstituted phenoxy or phenoxy substituted by chlorine or methyl, chlorine, alkylthio having 1 to 4 C atoms, phenylthio, alkylamino having 1 to 4 C atoms, dialkylamino having a total of 2 to 8 C atoms, morpholino, piperidino, piperazino, pyrrolidino or anilino, $R_6$ is alkyl having 1 to 4 C atoms, unsubstituted phenyl or phenyl substituted by chlorine or methyl and $R_7$ is alkoxy having 1 to 4 C atoms, alkoxyalkoxy having a total of 2 to 8 C atoms, alkylthio having 1 to 4 C atoms, unsubstituted phenoxy or phenoxy substituted by chlorine or methyl, cycloalkyloxy, alkylthio having 1 to 4 C atoms, unsubstituted phenylthio or phenylthio substituted by chlorine or methyl, alkylamino having 1 to 4 C atoms, dialkylamino having a total of 2 to 8 C atoms, morpholino, piperidino, piperazino, pyrrolidino or anilino, one of Z and $Z_o$ is hydrogen and the other is hydrogen or chlorine and the benzene nucleus A is unsubstituted or substituted by non-chromophoric substituents selected from alkyl, halogenalkyl, cyanoalkyl, hydroxyalkyl, alkoxyalkyl, phenoxyalkyl, carboxyalkyl, salts, esters and amides of carboxylalkyl, aralkyl, cycloalkyl, alkenyl, alkoxy, hydroxyalkoxy, alkoxyalkoxy, aralkoxy, phenoxyalkoxy, cyanoalkoxy, alkenyloxy, carboxy, sulfo, carboxylic and sulfonic acid salts, esters and amides, alkylsulfonyl, phenylsulfonyl, aryl, aryloxy and two adjacent radicals forming together the remaining members of an aromatic carbocyclic ring system.

2. A benzoxazolyl-stilbene according to claim 1, of the formula

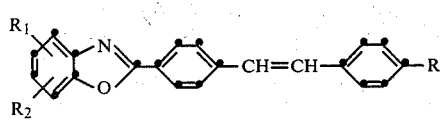

in which $R_1$ is hydrogen, unsubstituted alkyl having 1 to 4 C atoms, or alkyl having 1 to 4 C atoms which is substituted on the terminal C atom by a cyano or XOOC group, in which X is hydrogen, a salt-forming cation or alkyl having 1 to 5 C atoms; alkoxy having 1 to 4 C atoms; unsubstituted phenoxy or phenoxy substituted by 1 or 2 substituents from the group selected from chlorine, methyl and methoxy; chlorine, cyano, -COOX, in which X is as defined; hydroxyalkyl having 1 to 4 C atoms; phenyl; or $SO_2N(Y_1)(Y_2)$, in which $Y_1$ is hydrogen, alkyl having 1 to 6 C atoms, alkyl having 2 to 4 C atoms which is substituted on the terminal C atom by a dialkylamino group which has 1 to 4 C atoms per alkyl moiety and can be quaternised, or alkoxyalkoxy having 3 to 8 C atoms, hydroxyalkyl having 1 to 4 C atoms, alkoxyalkyl having a total of 3 to 8 C atoms, phenyl or benzyl and $Y_2$ is hydrogen, alkyl having 1 to 6 C atoms, hydroxyalkyl having 1 to 4 C atoms or alkoxyalkyl having a total of 3 to 8 C atoms, or $Y_1$ and $Y_2$ together with the nitrogen are a morpholino or piperidino radical; or $R_1$ is alkylsulfonyl having 1 to 6 C atoms, benzylsulfonyl or phenylsulfonyl or together with $R_2$ is a fused phenyl ring, $R_2$ is hydrogen, alkyl having 1 to 4 C atoms, alkoxy having 1 to 4 C atoms or chlorine or together with $R_1$ is a fused phenyl ring and R' is one of the ring systems of the formulae

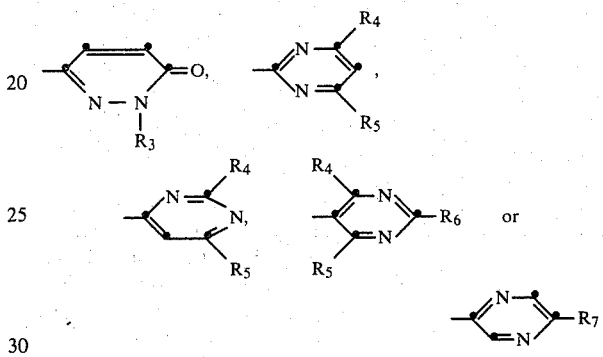

in which $R_3$ is hydrogen, alkyl having 1 to 4 C atoms, unsubstituted phenyl or phenyl substituted by chlorine or methyl, $R_4$ and $R_5$ independently of one another are hydrogen, alkyl having 1 to 4 C atoms, unsubstituted phenyl or phenyl substituted by chlorine or methyl, alkoxy having 1 to 4 C atoms, alkoxyalkoxy having a total of 3 to 8 C atoms, unsubstituted phenoxy or phenoxy substituted by chlorine or methyl, chlorine, alkylthio having 1 to 4 C atoms, phenylthio, alkylamino having 1 to 4 C atoms, dialkylamino having a total of 2 to 8 C atoms, morpholino, piperidino, piperazino, pyrrolidino or anilino, $R_6$ is alkyl having 1 to 4 C atoms, unsubstituted phenyl or phenyl substituted by chlorine or methyl and $R_7$ is alkoxy having 1 to 4 C atoms, alkoxyalkoxy having a total of 2 to 8 C atoms, alkylthio having 1 to 4 C atoms, unsubstituted phenoxy or phenoxy substituted by chlorine or methyl, cycloalkyloxy, alkylthio having 1 to 4 C atoms, unsubstituted phenylthio or phenylthio substituted by chlorine or methyl, alkylamino having 1 to 4 C atoms, dialkylamino having a total of 2 to 8 C atoms, morpholino, piperidino, piperazino, pyrrolidino or anilino.

3. A benzoxazolyl-stilbene according to claim 2, of the formula

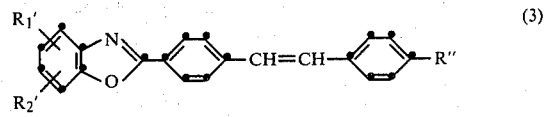

in which $R_1'$ is hydrogen, unsubstituted alkyl having 1 to 4 C atoms or alkyl having 2 to 4 C atoms which is substituted on the terminal C atom by a cyano group; alkoxy having 1 to 4 C atoms; unsubstituted phenoxy or phenoxy substituted by 1 or 2 substituents from the group selected from chlorine, methyl and methoxy;

alkoxyalkoxy having 3 to 8 C atoms; cyano; -COOX', in which X' is unsubstituted alkyl having 1 to 4 C atoms; phenyl; chlorine; alkylsulfonyl having 1 to 4 C atoms or phenylsulfonyl, $R_2'$ is hydrogen, chlorine, unsubstituted alkyl having 1 to 4 C atoms or unsubstituted alkoxy having 1 to 4 C atoms and R" is one of the ring systems of the formulae

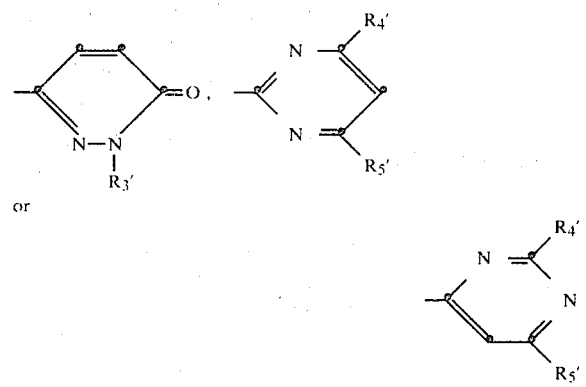

or

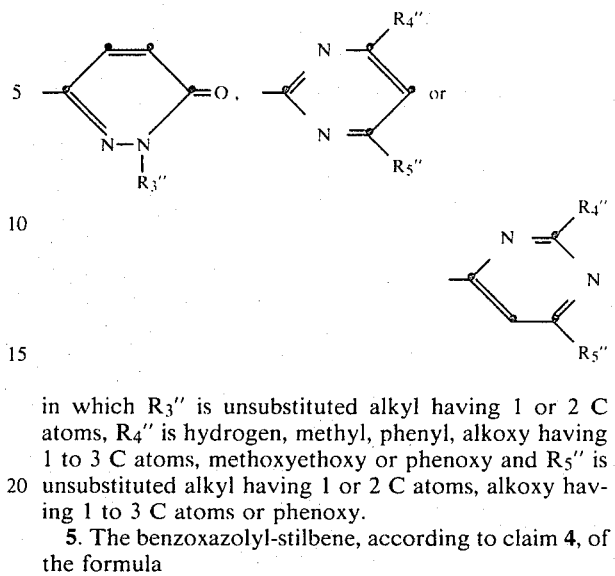

in which $R_3'$ is unsubstituted alkyl having 1 to 4 C atoms or phenyl, $R_4'$ is hydrogen, unsubstituted alkyl having 1 to 4 C atoms, unsubstituted phenyl or phenyl substituted by chlorine or methyl, chlorine, alkoxy having 1 to 4 C atoms, alkoxyalkoxy having a total of 3 to 5 atoms, unsubstituted phenoxy or phenoxy substituted by chlorine or methyl, alkylthio having 1 to 4 C atoms or phenylthio and $R_5'$ is hydrogen, unsubstituted alkyl having 1 to 4 C atoms, alkoxyalkoxy having 3 or 4 C atoms, alkoxy having 1 to 4 C atoms, unsubstituted phenyl or phenyl substituted by chlorine or methyl, unsubstituted phenoxy or phenoxy substituted by chlorine or methyl, alkylthio having 1 to 4 C atoms, phenylthio or chlorine.

4. A benzoxazolyl-stilbene according to claim 3, of the formula

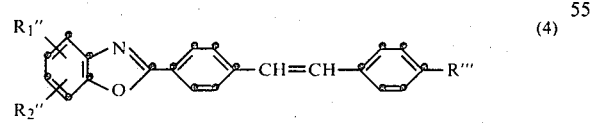 (4)

in which $R_1"$ is hydrogen; unsubstituted alkyl having 1 to 4 C atoms; cyanoethyl; methoxy; phenoxy; chlorine; cyano; alkoxyalkoxy having 3 to 8 C atoms; -COOX', in which X' is unsubstituted alkyl having 1 to 4 C atoms; phenyl or alkylsulfonyl having 1 to 3 C atoms, $R_2"$ is hydrogen, unsubstituted alkyl having 1 or 2 C atoms, methoxy or chlorine and R"" is one of the ring systems of the formulae in which $R_3"$ is unsubstituted alkyl having 1 or 2 C atoms, $R_4"$ is hydrogen, methyl, phenyl, alkoxy having 1 to 3 C atoms, methoxyethoxy or phenoxy and $R_5"$ is unsubstituted alkyl having 1 or 2 C atoms, alkoxy having 1 to 3 C atoms or phenoxy.

5. The benzoxazolyl-stilbene, according to claim 4, of the formula

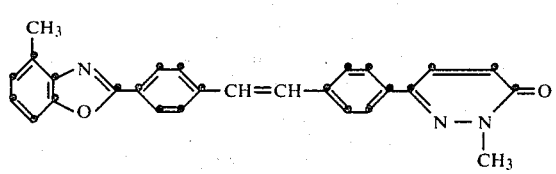

6. The benzoxazolyl-stilbene, according to claim 4, of the formula

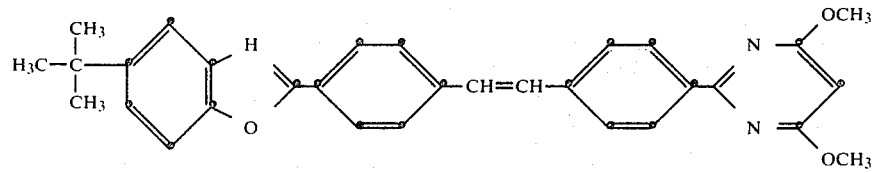

7. The benzoxazolyl-stilbene, according to claim 4, of the formula

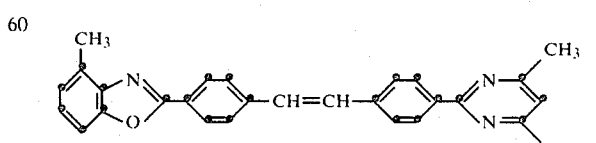

8. The benzoxazolyl-stilene, according to claim 4, of the formula

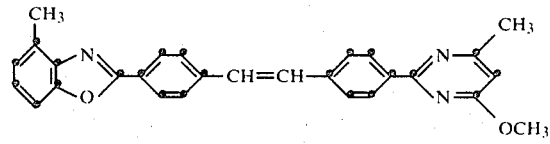

9. The benzoxazolyl-stilbene, according to claim 4, of the formula

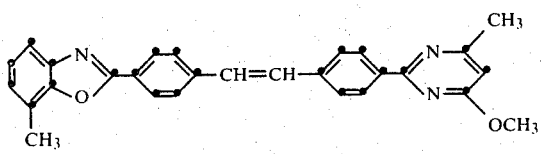

10. The benzoxazolyl-stilbene, according to claim 4, of the formula

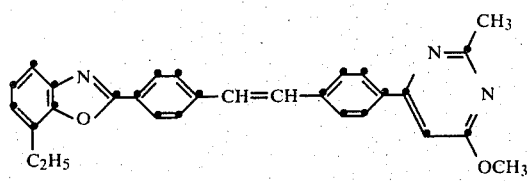

11. The benzoxazolyl-stilbene, according to claim 4, of the formula

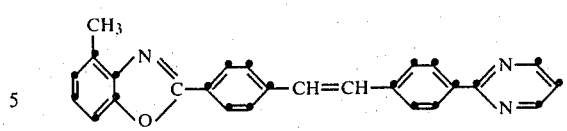

12. The benzoxazolyl-stilbene, according to claim 4, of the formula

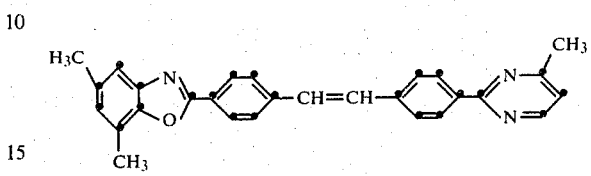

13. A process for the fluorescent brightening of high molecular weight synthetic, regenerated man-made and natural organic materials, which comprises incorporating in, or applying to the surface of, these materials a benzoxazolyl-stilbene as defined in claim 1 in an amount of 0.001 to 2%, based on the material to be subjected to fluorescent brightening.

14. A process according to claim 13, for the fluorescent brightening of polyester as the high molecular weight organic material.

* * * * *

UNITED STATES PATENT AND TRADEMARK OFFICE
CERTIFICATE OF CORRECTION

PATENT NO. : 4,297,234
DATED : OCTOBER 27, 1981
INVENTOR(S) : KURT BURDESKA ET AL

It is certified that error appears in the above—identified patent and that said Letters Patent is hereby corrected as shown below:

Claim 3, Column 35, line 29 reads:

"atoms, alkoxyalkoxy having a total of 3 to 5 atoms,"

Should read:

-- atoms, alkoxyalkoxy having a total of 3 to 5 C atoms, --

Signed and Sealed this

Second Day of March 1982

[SEAL]

*Attest:*

GERALD J. MOSSINGHOFF

*Attesting Officer*     *Commissioner of Patents and Trademarks*